(12) United States Patent
Graham et al.

(10) Patent No.: US 7,045,347 B2
(45) Date of Patent: May 16, 2006

(54) HELPER DEPENDENT ADENOVIRUS VECTORS BASED ON INTEGRASE FAMILY SITE-SPECIFIC RECOMBINASES

(75) Inventors: Frank L. Graham, Rome (IT); Michael A. Rudnicki, Ottawa (CA); Martina Anton, Vaterstetten (DE)

(73) Assignee: Advec, Inc., Ancaster (CA)

( * ) Notice: Subject to any disclaimer, the term of this patent is extended or adjusted under 35 U.S.C. 154(b) by 269 days.

(21) Appl. No.: 10/206,163

(22) Filed: Jul. 26, 2002

(65) Prior Publication Data

US 2003/0118554 A1 Jun. 26, 2003

Related U.S. Application Data

(63) Continuation-in-part of application No. 09/351,819, filed on Jul. 13, 1999, now abandoned, which is a continuation-in-part of application No. 09/251,955, filed on Feb. 17, 1999, now abandoned, which is a continuation-in-part of application No. 08/473,168, filed on Jun. 7, 1995, now Pat. No. 5,919,676.

(51) Int. Cl.
*C12N 15/861* (2006.01)
*C12N 7/00* (2006.01)
*C12N 7/01* (2006.01)
*A61K 31/713* (2006.01)
*A61K 48/00* (2006.01)

(52) U.S. Cl. .............. 435/320.1; 435/235.1; 435/455; 514/44; 424/93.2

(58) Field of Classification Search ............. 424/93.2; 435/457, 235.1, 320.1, 455; 514/44
See application file for complete search history.

(56) References Cited

U.S. PATENT DOCUMENTS

| | | | |
|---|---|---|---|
| 4,510,245 A | 4/1985 | Cousens et al. |
| 4,797,368 A | 1/1989 | Carter et al. |
| 4,920,209 A | 4/1990 | Davis et al. |
| 4,920,211 A | 4/1990 | Tibbetts et al. |
| 5,670,488 A | 9/1997 | Gregory et al. |
| 5,849,553 A | 12/1998 | Anderson et al. |
| 5,882,877 A | 3/1999 | Gregory et al. |
| 5,919,676 A | 7/1999 | Graham et al. |
| 6,080,569 A | 6/2000 | Graham et al. |

FOREIGN PATENT DOCUMENTS

| | | |
|---|---|---|
| WO | WO 93/19092 | 9/1939 |
| WO | WO 93/06223 | 4/1993 |
| WO | WO 93/19191 | 9/1993 |
| WO | WO 94/08026 | 4/1994 |
| WO | WO94/12649 | 6/1994 |
| WO | WO95/27071 | 12/1995 |
| WO | WO 96/13587 | 5/1996 |
| WO | WO 96/40955 | 12/1996 |
| WO | WO 97/05255 | 2/1997 |
| WO | WO 97/32481 | 9/1997 |
| WO | WO 99/41400 | 8/1999 |

OTHER PUBLICATIONS

Basak SK et al. "Modifying Adenoviral Vectors for Use as Gene-Based Cancer Vaccines", Viral Immun. vol. 17: p. 182-196. 2004.*
Dang, CV et al. "Gene Therapy and Translational Cancer Research", Clin. Cancer Res., vol. 5: p. 471-474, 1999.*
Gura T. "Systems for Identifying New Drugs Are Often Faulty", Science, vol. 278: p. 1041-1042, 1997.*
Orkin et al. Report and Recomendations . . . Gene Therapy. NIHPress. Dec. 7, 1995. p. 1-40.
Miller et al. FASEB. vol. 9:190-199, Feb. 1995.
Marshall. Science.369:1050-1055, Aug. 1995.
Culver et al. TIG. 10(5):174-178, May 1994.
Hodgson. Exp Opin Ther. Patents. 5(5):459-468, May 1994.
Neuwett et al Behavioral and Brain Sciences. 18:1-9 (1995).
Wolf Current Opinion in Neurobiology. 3:743-748 (1993).
McGrory et al Virology, 163:614-617 (1988).
Graham et al. Methods in Molecular Biology 7:109-128 (1991).
Kilby et al. Trends Genet. 9 413-421 (1993).
Yang et al. Proc Natl. Acad. Sci. USA 91:4407-4411 (May 1994).

(Continued)

*Primary Examiner*—David Guzo
*Assistant Examiner*—Michael D. Burkhart
(74) *Attorney, Agent, or Firm*—Joseph Fischer, Esq.; Beusse, Brownlee, Wolter, Mora & Maire, P.A.

(57) ABSTRACT

This invention provides helper-dependent adenovirus cloning vectors and helper adenoviruses, and methods for making and Using such preparations, wherein the helper adenoviruses contain recombinase target sites that are useful in reducing the level of contamination of helper virus in helper-dependent adenovirus vector preparations.

18 Claims, 20 Drawing Sheets

OTHER PUBLICATIONS

Anton, M., and F. L. Graham, 1995, Site-specific recombination mediated by an adenovirus vector expressing the Cre recombinase protein: a molecular switch for control of gene expression, J. Virol. 69: 4600-4606.

Araki, K., J. Araki, J. I. Miyazaki, and P. Vassali, 1995, Site-specific recombination of a transgene in fertilized eggs by transient expression of Cre recombinase. Proc. Nat'l. Acad. Sci. USA 92: 160-164.

Bett, A. J., L. Prevec, and F. L. Graham, 1993, Packaging capacity and stability of human adenovirus type 5 vectors. J. Virol. 67: 5911-5921.

Bett, A. J., W. Haddara, L. Prev, and F. L. Graham, 1994, An efficient and flexible system for construction of adenivorus vectors with insertions or deletions in early region 1 and 3. Proc. Nat'l. Acad. Sci. USA 91:8802-8806.

Brody, H. A. Jaffe, N. T. Eissa, and C. Danel. 1994. Administration of an adenivorus containing the human CFTR cDNA to the respiratory tract of individuals with cystic fibrosis, Nature Genetics 8: 42-51.

DiSanto, J. P., W. Mueller, D. Guy-Grand, A. Fischer, and K. Rajewsky, 1995, Lymphoid development in mice with a targeted deletion of the interleukin 2 receptor chain, Proc. Nat'l. Acad. Sci. USA 92: 377-381.

Gage, P J., B. Sauer, M. Levin and J. C. Glorioso. 1992 A cell-free recombination system for site-specific integration of multigenic shuttle plasmids into the herpes simplex virus type 1 genome. J. Virol. 66: 5509-5515.

Graham, F. L. and L. Prevec. 1991. Manipulation of adenovirus vectors. In Murray E.J. (ed.), Methods in Molecular Biology The Humana Press Inc Clifton, N.J. vol. 7 (Gene Transfer and Expression Protocols): 109-128.

Graham F. L. and L. Prevec. 1992. Adenovirus-based expression vectors and recombinant vaccines. in: Vaccines. New Approaches in Immunological Problems., ed. Ellis, R.W. Butterworth-Heinemann, Boston, MA: 363-390.

Graham F. L., J. Smiley, W C. Russel and R. Naim. 1977 Characteristics of a human cell line transformed by DNA from human adenovirus type 5., J. Gen. Virol. 36: 59-72.

Gu, H. J. D March, P.C. Orban, H. Mosemann and K Rajewsky 1994. Deletion of a DNA polymerase B gene segment in T cells using cell type-specific gene targeting. Science 265 103-106.

Kilby, N. J., M. R. Snaith, and J. A. H. Murray. 1993. Site-specific recombinases: tools for genome engineering Trends Genet. 9: 413-421.

Metzger, D., J. Clifford, H. Chiba and P. Chambon. 1995. Conditional site-specific recombination in mammalian cells using a ligand-dependent chimeric Cre protein. Proc. Nat'l. Acad. Sci. USA 92: 6991-6995.

Pichel, J. G., Lakso, and H. Westphal. 1993. Timing of SV40 oncogene activation by site-specific recombination determines subsequent tumor progression during murine lens development. Oncogene 8: 3333-3342.

Sauer, B. 1994. Site-specific recombination: developments and applications. Cur. Opin. Biotech. 5: 521-527.

Sauer, Brian and Nancy Henderson. 1988. Site-specific DNA recombination in mammalian cells by the Cre recombinase of bacteriophage Pl. Proc. Nat'l. Acad. Sci. USA 85: 5166-5170nn.

Sauer, B. and N. Henderson. 1989. Cre-stimulated recombination of IoxP-containing DNA sequences placed into the mammalian genome. Nucl. Acids Res. 17: 147-161.

Sauer, B., and N. Henderson. 1990. Targeted insertion of exogenous DNA into the eukaryotic genome by the Cre recombinase. The New Biologist 2: 441-449.

Sauer, B., M. Whealy, A. Robbins and L. Enquist. 1987. Site-specific insertion of DNA into a pseudorabies virus vector. Proc. Nat'l. Adac. Sci. USA 84: 9108-9112.

Smith A. J. H., M. A. DeSousa, B. Kwabi-Addo, A. Heppel-Parton, H. Impey, and P. Rabbits. 1995. A site-directed chromosomal translocation induced in embryonic stem cells by Cre-IoxP recombination. Nature Genetics 9: 376-385.

Rabbits. 1995. A site-directed chromosomal translocation induced in embryonic stem cells by Cre-IoxP recombination. Nature genetics 9: 376-385.

Sternberg, N., B. Sauer, R. Hoess, and K. Abremski. 1986. Bacteriophase P1 cre gene and its regulatory region; Evidence for multiple promotors and for regulation by DNA methylation., J. Mol. Biol. 187: 197-212.

Van Deursen, J., M. Fornerod, B. Van Rees, and G. Grosveld. 1995. Cre-mediated site specific translocation between non-homologous mouse chromosomes. Proc. Nat'l. Acad. Sci. USA 92: 7376-7380.

Mittal, S.K., McDermott, M.R., Johnson, D.C., Prevec, L. and F. L. Graham. 1993. Monitoring foreign gene expression by a human adenovirus-based vector using the firefly luciferase gene as a reporter, Virus Research, 28: 67-90.

Hanke, T., Frank L. Graham, Kenneth L. Rosenthal and David C. Johnson. 1991. Identification of an immunodominant cytotoxic t-lymphocyte recognition site in glycoprotein B of herpes simplex virus by using recombinant adenovirus vectors and synthetic peptides. 1991. J. of Virology, 65: 1177-1186.

Graham, F.L., 1987. Growth of 293 cells in suspension culture. J. Gen. Virol. 68: 937-940.

Quantin, B., Leslie D. Pericaudet, Shahragim Tajbakhsh and Jean-Louis Mandel. 1992. Adenovirus as an expression vector in muscle cells in vivo. Proc. Nat'l. Acad. Scie. 89: 2581-2584.

Bett, A.J., Wael Haddara, Ludvik Prevec and Frank L. Graham, 1994. Proc. Nat'l. Acad. Sci. 91: 8802-8806.

Rosenfeld, M.A. et al., 1992. In vivo transfer of the human cystic fibrosis transmembrane conductance regulator gene to the airway epithelium, Cell. 68: 143-155.

W. J. McGrory, D. S. Baulista and F. L. Graham. 1998. A simple technique for the resue of early region 1 mutations into infectious human adenovirus type 5, Virology 163: 614-617.

Wang, P., Anton, F. L. Graham and S. Bacchetti. High Frequency recombination between IoxP sites in human chromosomes mediated by an adeniovorus vector expressing Cre recombinase.

Kornberg & Baker (DNA Replication, Chapter 21-6, pp 806-817, W. H. Freeman, NY $2^{nd}$ Edition, 1992.

Russ, Andreas P., et al., 1996,. Self-deleting Retrovirus Vectors for Gene Terapy, J. of Virology, pp. 4927-4932.

RG Crystal, Science,, "Transfer of Genes to Humans: Early Lessons and Obstacles to Success," 1995095V.

N. Miller et al., FASEB Journal, "Targeted vectors for gene Therapy," 1995, vol. 9, pp. 190-199.

MP Deonarain, Exp. Opin. Ther. Patents, "Ligand-targeted receptor-mediated vector for gene therapy," 1998, 8(1):53-69.

Anderson et al., 1998, Nature, 392(supp): 25-30.

Verma et al., 1997, Nature, 389: 239-242.

Gudrun Schiedner, et al., 1998. Genomic DNA transfer with a high-capacity adenovirus vector results in improved in vivo gene expression and decreased toxicity. Nature Genetics 18: 180-183.

Manal A. Morsy, et al., 19998. An adenoviral vector deleted for all viral coding sequences results in enhanced safety and extended expression of a leptin transgene. Proc. Nat'l. Acad. Sci. USA 95: 7866-7871.

Stephen Hardy, et al., 1997. Construction of Adenovirus Vectors through Cre-lox Recombination. Jour. Virol. 71: 3 1842-1849.

Parks, et al., 1996. A helper-dependent adenovirus vector system: removal of helper virus by Cre-mediated excision of the viral packaging signal. Pro. Nat'l. Acad. Sci. USA 93: 13565-13470.

A. Kass-Eisler, L. Leinwand, J. Gall, B. Bloom and E. Falck-Pedersen. 1996. Circumventing the immune response to adenovirus-mediated gene therapy. Gene Terapy 3: 154-6879.s.

Roy, S., Shirley, P. S. McClelland, A. and Kaleko, M. 1998. Circumvention of Immunity to the Adenovirus Major Coat Protein Hexon. J. Virology 72: (8) 6875-6879.

Mack, Charles A. et al. 1997. Circumvention of Anti-Adenivirus Neutralizing Immunity by Administration of an Adeniviral Vector of an Alternate Serotype. Hum. Gene Therapy 8: 99-109.

* cited by examiner

CRE MEDIATED EXCISION
OF AD SEQUENCES FLANKED BY LOX

FIGURE 2
HELPER DEPENDENT VECTORS USING CRE/LOX
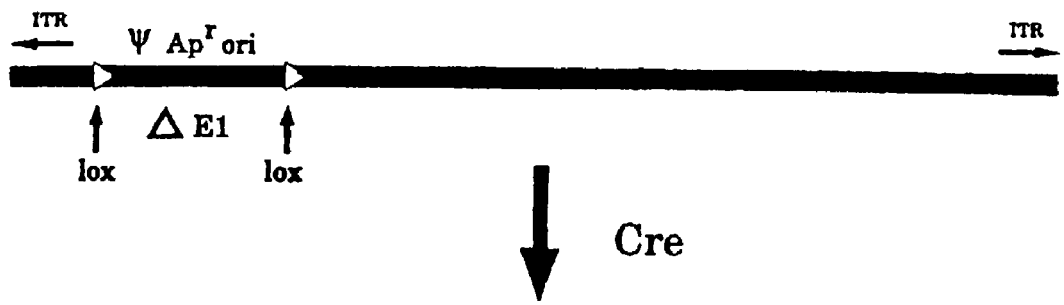
UNPACKAGEABLE HELPER VIRUS DNA
PROVIDES ESSENTIAL VIRAL FUNCTION IN TRANS (HELPER FUNCTIONS) FOR:
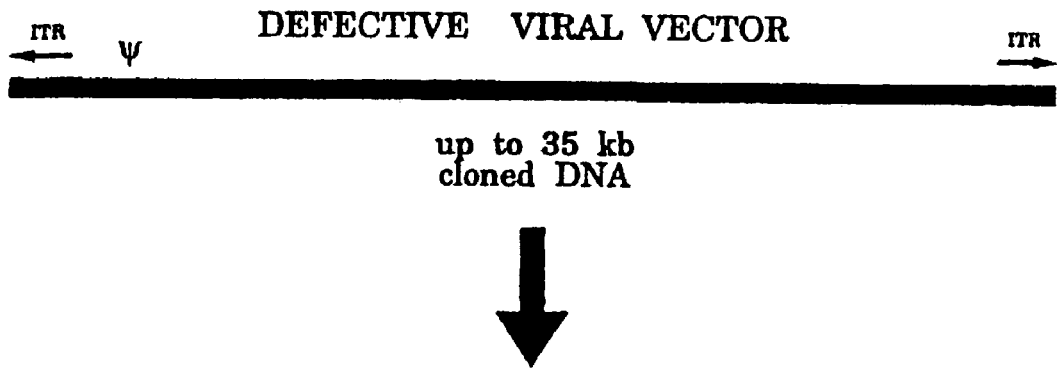
REPLICATION OF BOTH VECTOR & HELPER DNA: PACKAGING OF VECTOR DNA ONLY

CONSTRUCTION OF AN AD5 VECTOR WITH MOST OF THE AD GENOME DELETED

FIGURE 5 Cotransfection of 293Cre cells with pBG17Lox2 and pADHDV1 DNA: generation of coreplicating helper and helper-dependent viruses AdBG17ψ⁻ and AdHDV1

FLP: a 43 kD site specific recombinase
(encoded by 2μ plasmid of yeast)

FLP acts on FRT:

GAAGTTCCTATAC TTTCTAGA GAATAGGAACTTC C GAATAGGAACTTC

SEQ NO:2

FLP catalyzes site specific recombination
between FRT sites

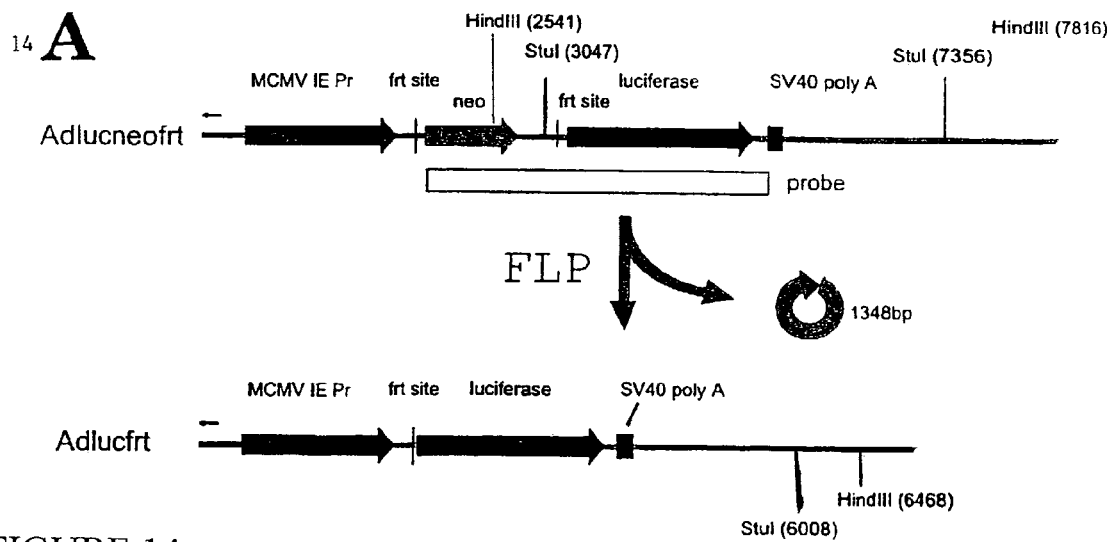
FIGURE 14
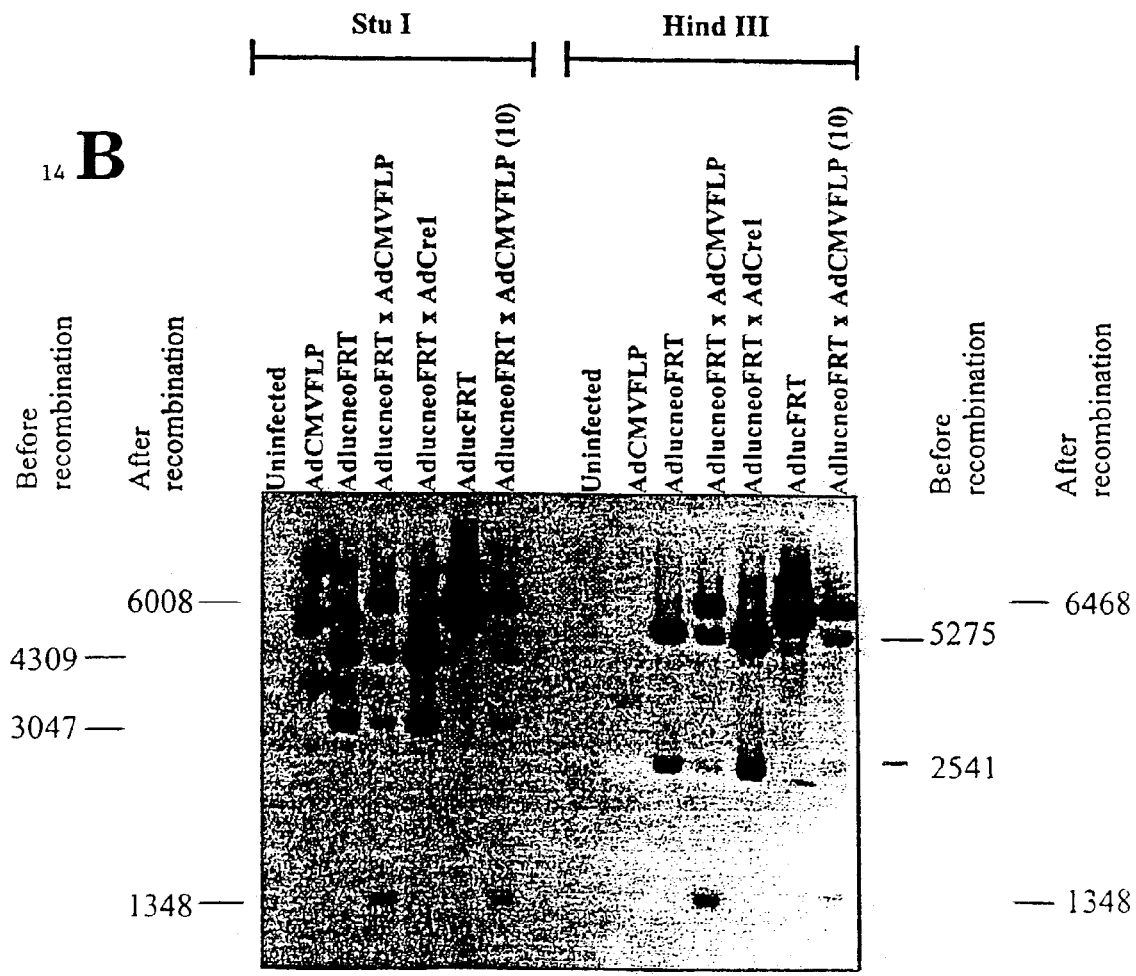

CONSTRUCTION OF PLASMID pCBFLPHY
FOR ISOLATION OF CELL LINES EXPRESSING FLP

Construction of a helper virus with ψ flanked by FRT sites and effect of FLP-mediated excision of ψ.

FLP mediated excision of Ad DNA flanked by FRT sites
in AdCBFRT2 infected 293 cells expressing FLP Southern blot showing FLP mediated excision of DNA flanked by FRT sites in AdCBFRT2 infected 293 cells expressing FLP

HELPER DEPENDENT ADENOVIRUS VECTORS BASED ON INTEGRASE FAMILY SITE-SPECIFIC RECOMBINASES

This application is a continuation-in-part of application Ser. No. 09/351,819, filed Jul. 13, 1999, now abandoned, which is a continuation-in-part of application Ser. No. 09/251,955, filed on Feb. 17, 1999, now abandoned, which is a continuation-in-part of application Ser. No. 08/473,168, filed on Jun. 7, 1995, issued Jul. 6, 1999 as U.S. Pat. No. 5,919,676. The benefit of priority under 35 USC 119 and/or 120 is claimed for all of the above applications, and each of these applications is hereby incorporated by reference.

FIELD OF THE INVENTION

The present invention relates to adenovirus vectors that have increased utility for gene transfer into mammalian cells. The vector systems described have increased capacity for insertion of foreign DNA and improved safety.

BACKGROUND OF THE INVENTION

Parent application Ser. No. 08/250,885, filed on May 31, 1994 and its parent application Ser. No. 08/080,727 disclose and claim a genus of adenovirus(Ad)-derived cell expression vectors having excellent potential as live recombinant vaccines and as transducing vectors for gene therapy. In the human Ad genome, early region 1 (E1), E3, and a site upstream of E4 have been utilized as sites for introducing foreign DNA sequences to generate adenovirus recombinants. In the absence of compensating deletions in E1 or E3, a maximum of about 2 kb can be inserted into the Ad genome to generate viable virus progeny. The E1 region is not required for viral replication in complementing 293 cells and up to 3.2 kb can be deleted in this region to generate conditional helper independent vectors with a capacity of 5.0–5.2 kb. In the E3 region, which is not required for viral replication in cultured cells, deletions of various sizes have been utilized to generate nonconditional helper independent vectors with a capacity of up to 4.5–4.7 kb.

The maximum capacity for inserts of foreign DNA in currently available helper independent Ad vectors such as those described in the parent applications is approximately 8 kb. This limited capacity arises from the use of Ad vectors which have deletions of E1 and E3 sequences and from the fact that most other regions of the viral genome must be retained in order that the viral vector may be propagated without the need for a helper virus.

Besides this limited capacity for insert DNA, previous vectors retain most of the viral genome, making it possible for expression of viral genes in transduced cells or in inoculated animals, including humans, which can result in toxic or other untoward effects. In addition, previous viral vectors can recombine with Ad sequences present in cells used for propagation of the vectors or with Ad sequences that may be present in inoculated animals. Therefore, it is an objective of this invention to provide Ad cloning vectors from which all or most viral genes have been removed and which have increased safety and capacity for larger insertions compared to currently available vectors.

SUMMARY OF THE INVENTION

It is a goal of this invention to provide a simple and useful system by which high capacity Ad5 cloning vectors may be developed. As demonstrated in concurrently filed application Ser. No. 08/486,549, entitled "Adenoviruses for Control of Gene Expression", provision of Cre recombinase in Ad infected cells can catalyze excision or rearrangement of viral DNA sequences that contain the target sites (lox P) for Cre mediated site specific recombination. In the present invention, use is made of this knowledge to construct Ad5 genomes in which the viral DNA packaging signals can be excised from the viral genome by action of Cre, FLP or other recombinase. Said excision of said packaging signal results in a viral DNA that is unable to package into virion particles. Such a viral DNA, though unable to package into virions, may encode viral functions that provide complementing functions for replication of a second, viral "vector", that lacks substantial portions of the viral genome so that in coinfected cells, though both helper and vector DNAs may replicate, only the vector DNA can be packaged into virions.

One embodiment of the present invention provides a bacterial plasmid comprising a circularized modified human adenovirus type 5 (Ad5) or other adenoviral genome that contains sequences that can be recognized and acted upon by a site specific recombinase known as Cre, FLP, or any other known recombinase which specifically recognizes a target recombination site. Said bacterial plasmid is able to generate infectious Ad5 carrying the modified sequences including the sequences that can be recognized by the site-specific recombinase. The structure of the modified sequences in the bacterial plasmid and in viruses generated from said plasmid is such that recombination catalyzed by the site-specific recombinase results in excision of sequences, known as the packaging signal, near the left end of the Ad5 genome, that are required for packaging of Ad5 or other adenoviral DNA into infectious virion particles. Optionally, certain regions of the plasmid and resulting viruses may be deleted, such as sequences from E1 or E3 that can be omitted from the viral genome without preventing the viral genome from replicating in such cells as may be permissive for replication of said viral genome in the form of infectious virus.

A second embodiment of the invention provides a bacterial plasmid comprising approximately 340 base pairs from the left end of the Ad5 or other adenoviral genome, including the left end terminal repeat sequences of said genome and the packaging signal sequences thereof and the right terminal repeat sequences of the Ad5 or other adenoviral genome. The left end of the left terminal repeat sequence is joined in "head to tail" configuration with the right end of the right terminal repeat viral DNA sequences. DNA sequences between approximately nucleotide 340 near the left end and approximately nucleotide 35,800 near the right end of the genome, are substituted with restriction enzyme sites suitable for insertion of foreign DNA sequences of up to about 35,000 base pairs in length. Naturally, those skilled in the art will appreciate from this disclosure that other configurations may be used, such as that illustrated in FIG. 6.

A third embodiment of the invention provides a bacterial plasmid comprising approximately 340 base pairs from the left end of the Ad5 or other adenoviral genome, including the left end terminal repeat sequences of said genome and the packaging signal sequences thereof and the right terminal repeat sequences of the Ad5 or other adenoviral genome. The left end of the left terminal repeat sequence and the right end of the right terminal repeat sequence are joined to plasmid DNA sequences and can be cleaved from said plasmid DNA sequences by restriction enzyme digestion. Viral DNA sequences between approximately nucleotide 340 near the left end and approximately nucleotide 35,800 near the right end of the genome, are substituted with restriction enzyme sites suitable for insertion of foreign DNA sequences of up to about 35,000 base pairs in length.

A fourth embodiment of the invention provides a mammalian cell line, such as a human cell line, that expresses a recombinase enzyme such as Cre, FLP, combinations thereof or other recombinases. Alternatively, Cre, FLP or other site-specific recombinase functions may be provided by an Ad5 or other adenoviral derived vector that expresses the recombinase in suitable cells.

Other embodiments of the present invention include Ad genome constructs, known as "vectors", containing substantial deletions of viral DNA sequences that are substituted with large insertions of foreign DNA, 20–35 kb in length. Such genomes are unable to replicate as viruses in the absence of viral products provided by a second virus, hereafter called a "helper" virus.

One specific embodiment of the invention is a helper virus that can be designed, propagated, and used in such a way that when employed to support replication of a second virus, the vector, from which substantial portions of the viral genome have been deleted and substituted with foreign DNA, said "helper" virus DNA is unable to be packaged into infectious virions.

BRIEF DESCRIPTION OF THE DRAWINGS

FIG. 2 is a diagrammatic representation of a method to generate helper dependent viral vectors using Cre-mediated excision of the packaging signal to prevent packaging of the helper virus DNA.

FIG. 14A Schematic diagram illustrating the structures of products of FLP mediated recombination in cells coinfected with Adlucneofrt and AdFLP.

FIG. 14B Results of Southern blot hybridization analysis of DNA extracted from cells infected or coinfected with Adlucneofrt and AdFLP.

DETAILED DESCRIPTION OF THE PREFERRED EMBODIMENTS

Figure 1:
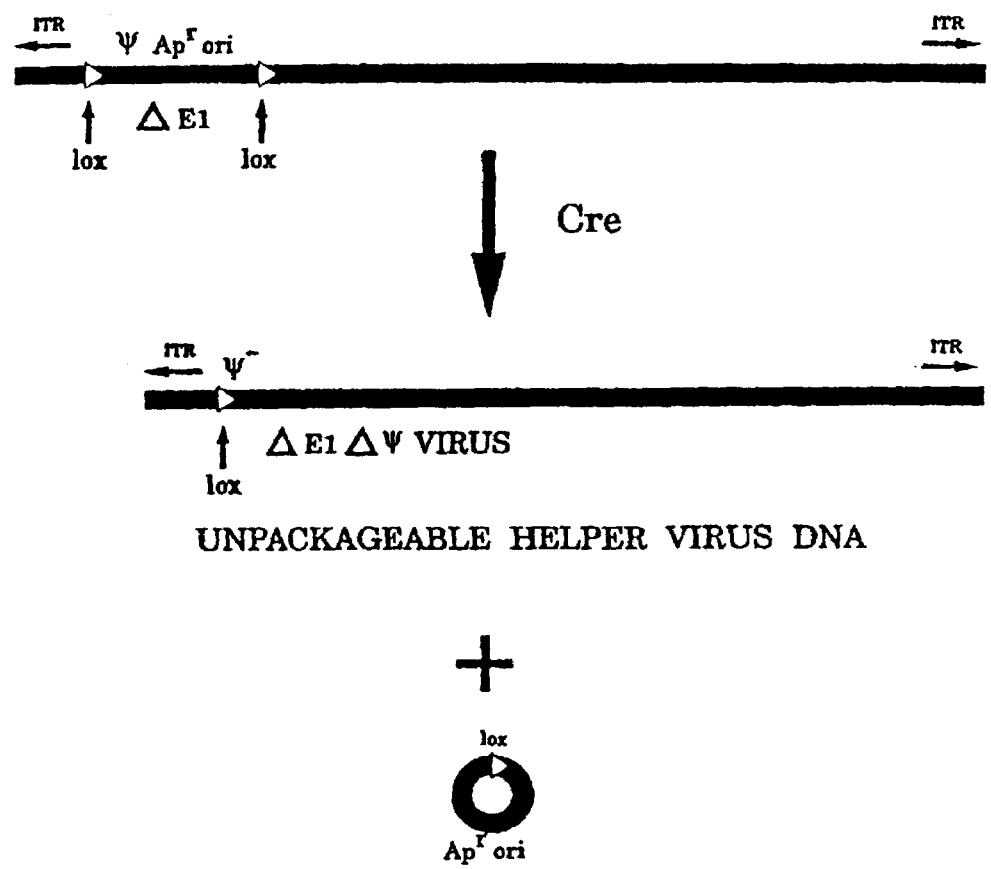
FIG. 1 is a diagrammatic representation of Cre-mediated excision of DNA from a viral vector in which the packaging signal is flanked by lox P sites.

Any publications referenced herein are hereby incorporated by reference in this application in order to more fully describe the state of the art to which the present invention pertains.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

The terms used herein are not intended to be limiting of the invention. For example, the term "gene" includes cDNAs, RNA, or other polynucleotides that encode gene products. "Foreign gene" denotes a gene that has been obtained from an organism or cell type other than the organism or cell type in which it is expressed; it also refers to a gene from the same organism that has been translocated from its normal situs in the genome. In using the terms "nucleic acid", "RNA", "DNA", etc., we do not mean to limit the chemical structures that can be used in particular steps. For example, it is well known to those skilled in the art that RNA can generally be substituted for DNA, and as such, the use of the term "DNA" should be read to include this substitution. In addition, it is known that a variety of nucleic acid analogues and derivatives is also within the scope of the present invention. "Expression" of a gene or nucleic acid encompasses not only cellular gene expression, but also the transcription and translation of nucleic acid(s) in cloning systems and in any other context. The term "recombinase" encompasses enzymes that induce, mediate or facilitate recombination, and other nucleic acid modifying enzymes that cause, mediate or facilitate the rearrangement of a nucleic acid sequence, or the excision or insertion of a first nucleic acid sequence from or into a second nucleic acid sequence. The "target site" of a recombinase is the nucleic acid sequence or region that is recognized (e.g., specifically binds to) and/or acted upon (excised, cut or induced to recombine) by the recombinase. The term "gene product" refers primarily to proteins and polypeptides encoded by other nucleic acids (e.g., non-coding and regulatory RNAs such as tRNA, sRNPs). The term "regulation of expression" refers to events or molecules that increase or decrease the synthesis, degradation, availability or activity of a given gene product.

The present invention is also not limited to the use of the cell types and cell lines used herein. Cells from different tissues (breast epithelium, colon, lymphocytes, etc.) or different species (human, mouse, etc.) are also useful in the present invention.

It is important in this invention to detect the generation and expression of recombinant nucleic acids and their encoded gene products. The detection methods used herein include, for example, cloning and sequencing, ligation of oligonucleoltides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Sequencing may be carried out with commercially available automated sequencers utilizing labeled primers or terminators, or using sequencing gel-based methods. Sequence analysis is also carried out by methods based on ligation of oligonucleotide sequences which anneal immediately adjacent to each other on a target DNA or RNA molecule (Wu and Wallace, *Genomics* 4: 560–569 (1989); Landren et al., *Proc. Natl. Acad. Sci.* 87: 8923–8927 (1990); Barany, F., *Proc. Natl. Acad. Sci.* 88: 189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperatures permits the ligation reaction to be conducted with high stringency (Barany, F., *PCR Methods and Applications* 1: 5–16 (1991)).

The hybridization reactions may be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

The detection oligonucleotide probes range in size between 10–1,000 bases. In order to obtain the required target discrimination using the detection oligonucleotide probes, the hybridization reactions are generally run between 20°–60° C., and most preferably between 30°–50° C. As known to those skilled in the art, optimal discrimination between perfect and mismatched duplexes is obtained by manipulating the temperature and/or salt concentrations or inclusion of formanide in the stringency washes.

The cloning and expression vectors described herein are introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by references, and in Ausubel et al., *Current Protocols in Molecular Biology*, John Wiley and Sons, Baltimore, Md. (1989), which is also hereby incorporated by reference. The methods include, for example, stable or transient transfection, lipofection, electroporation and infection with recombinant viral vectors.

The protein products of recombined and unrecombined coding sequences may be analyzed using immune techniques. For example, a protein, or a fragment thereof is injected into a host animal along with an adjutant so as to generate an immune response. Immunoglobulins which bind the recombinant fragment are harvested as an antiserum, and are optionally further purified by affinity chromatography or other means. Additionally, spleen cells may be harvested from an immunized mouse host and fused to myeloma cells to produce a bank of antibody-secreting hybridoma cells. The bank of hybridomas is screened for clones that secrete immunoglobulins which bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Nucleic acid sequences capable of ultimately expressing the desired variant polypeptides are formed from a variety of different polynucleotides (genomic or cDNA, RNA, synthetic olignucleotides, etc.) as well as by a variety of different techniques.

The DNA sequences are expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors contain selection markers (e.g., markers based on tetracycline resistance or hygromycin resistance) to permit detection and/or selection of those cells transformed with the desired DNA sequences. Further details can be found in U.S. Pat. No. 4,704,362.

Polynucleotides encoding a variant polypeptide include sequences that facilitate transcription (expression sequences) and translation of the coding sequences such that the encoded polypeptide product is produced. Construction of such polynucleotides is well known in the art.

For example, such polynucleotides include a promoter, a transcription termination site (polyadenylation site in eukaryotic expression hosts), a ribosome binding site, and, optionally, an enhancer for use in eukaryotic expression hosts, and optionally, sequences necessary for replication of a vector.

*E. Coli* is one prokaryotic host useful particularly for cloning DNA sequences of the present invention. Other microbial hosts suitable for use include bacilli, such as *Bacillus subtilus*, and other enterobacteriaceae, such as *Salmonella, Serratia*, and various *Pseudomonas* species. Expression vectors are made in these prokaryotic hosts which will typically contain expression control sequences compatible with the host cell (e.g., an origin of replication). In addition, any number of a variety of well-known promoters are used, such as the lactose promoter system, a tryptophan (Trp) promoter system, a beta-lactamase promoter system, or a promoter system from phage lambda. The promoters typically control expression, optionally with an operator sequence, and have ribosome binding site sequences, for example, for initiating and completing transcription and translation.

Other microbes, such as yeast, are used for expression. *Saccharomyces* is a suitable host, with suitable vectors having expression control sequences, such a promoters, including 3-phosphoglycerate kinase or other glycotic enzymes, and an origin of replication, termination sequences, etc. as desired.

In addition to microorganisms, mammalian tissue cell culture is used to express and produce the polypeptides of the present invention. Eukaryotic cells are preferred, because a number of suitable host cell lines capable of secreting intact human proteins have been developed in the art, and include the CHO cell lines, various COS cell lines, HeLa cells, myeloma cell lines, Jurkat cells, and so forth. Expression vectors for these cells include expression control sequences, such as an origin of replication, a promoter, an enhancer, an necessary information processing sites, such as ribosome binding sites, RNA splice sites, polyadenylation sites, and transcriptional terminator sequences. Preferred expression control sequences are promoters derived from immunoglobin genes, SV40, Adenovirus, Bovine Papilloma Virus, and so forth. The vectors containing the DNA segments of interest (e.g., polypeptides encoding a variant polypeptide) are transferred into the host cell by well-known methods, which vary depending on the type of cellular host. For example, calcium chloride transfection is commonly utilized for prokaryotic cells, whereas calcium phosphate treatment or electroporation is useful for other cellular hosts.

The method lends itself readily to the formulation of test kits for use in diagnosis. Such a kit comprises a carrier compartmentalized to receive in close confinement one or more containers wherein a first container contains reagents useful in the localization of the labeled probes, such as enzyme substrates. Still other containers contain restriction enzymes, buffers etc., together with instructions for use.

The recombinant Ad vectors described herein are significantly different from previously described constructs. They combine the use of vectors having deletions of all or most of the viral genes with helper viruses that are designed so that, when used in coinfections with vector viruses, said helper viruses are able to complement the growth of the vectors but are unable to package their viral DNA into infectious virions. Thus vector viruses can be prepared substantially free of helper virus.

For viral DNA replication and packaging of viral DNA into virion particles, only three regions of the viral DNA are known to be required in cis. These are the left inverted terminal repeat, or ITR, (bp 1 to approximately 103) the packaging signals (approximately 194 to 358 bp) (Hearing and Shenk, 1983, Cell 33: 695–703; Grable and Hearing 1992, J. Virol. 64: 2047–2056) and the right ITR. All other regions of the viral genome appear to be required only to produce viral products that act in trans to allow viral replication and production of infectious viruses. Thus if all essential viral proteins and RNA could be provided by a helper virus, a vector could be designed and constructed that could have most of the viral DNA deleted save for those sequences mentioned above that are required in cis for viral DNA replication and packaging.

A problem with helper dependant vectors has been that preparations of such vectors are invariably contaminated with helper virus and it is technically very difficult to separate the helper from the vector. In the main embodiments of the present invention, the helper virus is designed to have two lox P sites, two FRT sites or like recombinase recognition target sites near the left end of the genome, one inserted at approximately 189 bp from the extreme left end of the viral DNA, and the second, in parallel orientation with the first, situated rightward of the packaging signals, ie rightward of bp 358 (diagrammed in FIG. 1 with lox P sites as illustrative of the general method of this invention). This virus will be able to replicate in cells that are normally permissive for growth of Ad5. However, in cells that express the Cre recombinase, or in the presence of a second virus that expresses Cre recombinase, excision of sequences between the lox P sites of the helper virus DNA removes the packaging signal, and the resulting viral DNA fails to package into infectious viral particles. Therefore, in cells coinfected with said helper and with a second virus, a vector from whose genome has been deleted all or most of the viral DNA sequences that are normally required for expression of viral products necessary in trans for viral replication, both vector and helper viral genomes will replicate, but only the vector DNA that retains the packaging signal will be packaged into virions (FIG. 2). Using FLP recombinase and FRT target recognition sites or combinations of such sites and Cre and lox P or other recombinase/target sites, similar results are achieved.

Figure 3:
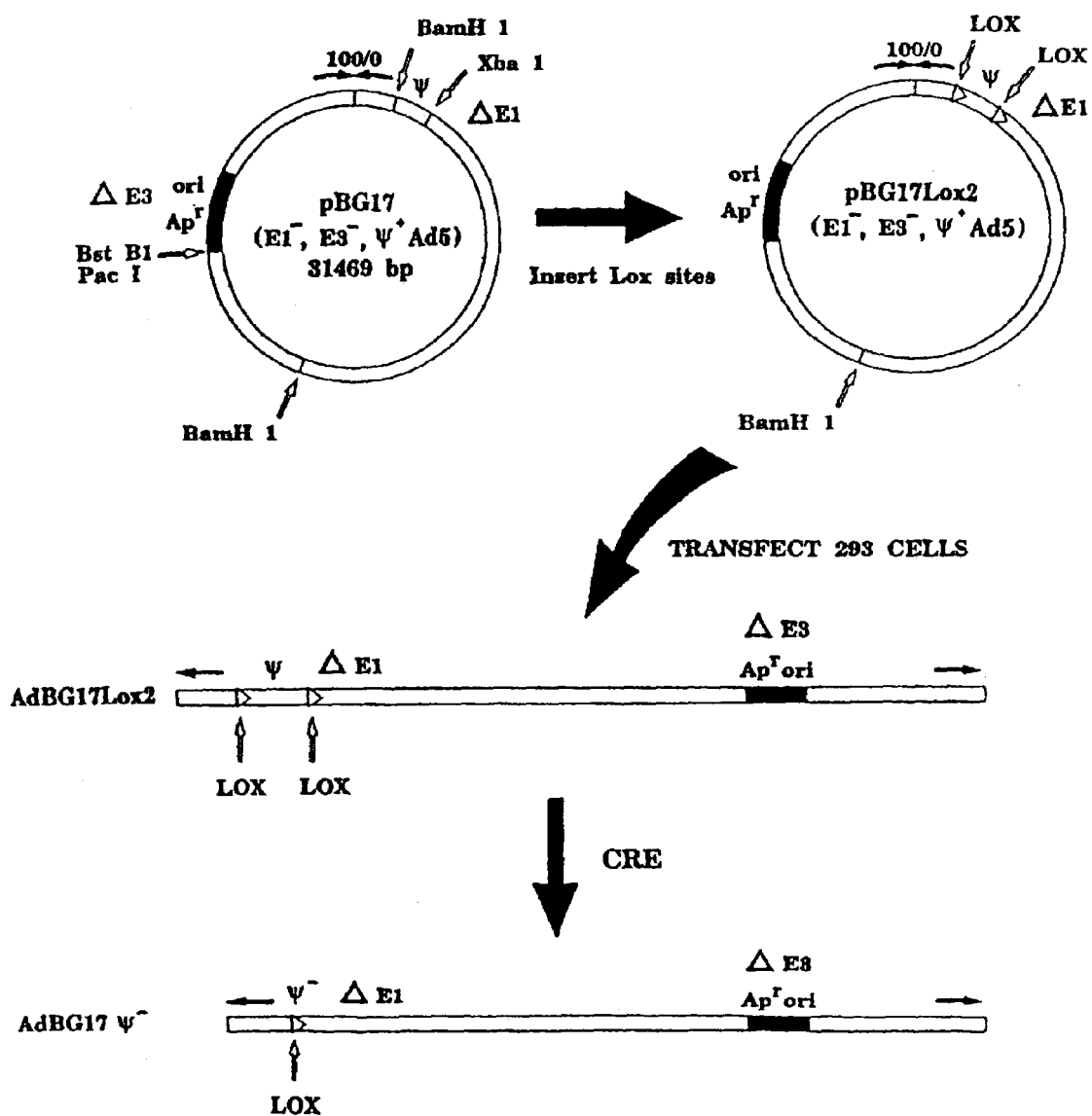
FIG. 3 is a diagrammatic representation of a plasmid derived from pBHG10 into which lox P sequences have been introduced at positions flanking the packaging signal.
Figure 4:
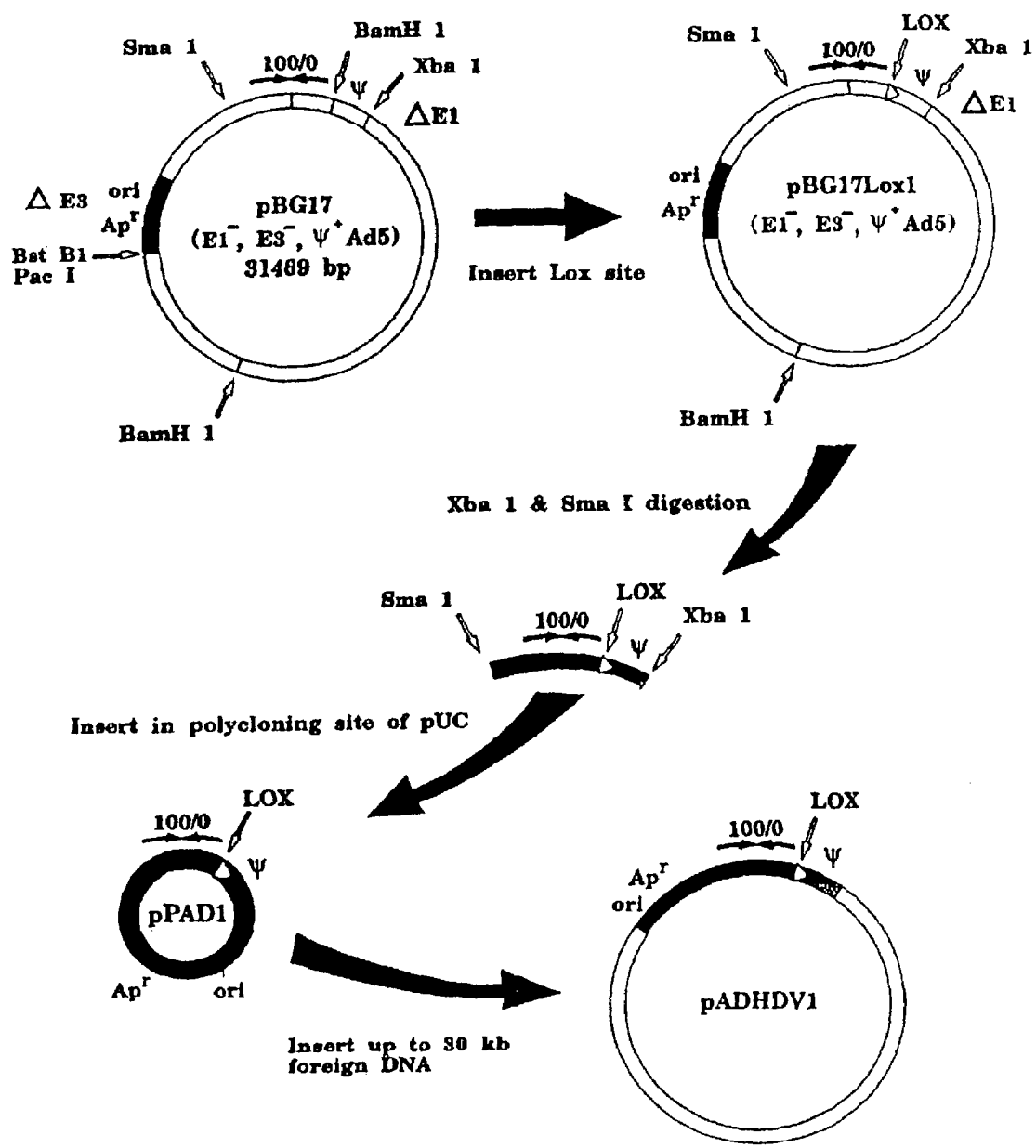
FIG. 4 is a diagrammatic representation of a plasmid derived from pBHG10 from which most of the viral DNA has been deleted save for the left and right ITRs and the packaging signal.

In one embodiment of the invention, the helper virus is derived from a plasmid similar to those described in the parent applications and as illustrated in FIGS. 3 and 4. In these examples, the Ad5 genome or another adenoviral genome is present as a circular molecule containing a bacterial plasmid derived origin of DNA replication (designated "ori") and a bacterial antibiotic resistance coding sequence ("AP'") conferring to bacteria carrying said molecule resistance to ampicillin. In this example in which said circular form of the Ad5 genome is designated pBG17, viral sequences from regions E1 and E3 have been deleted from the viral genome, but this example is not meant to be limiting since other deletions or no deletions may equally be engineered in the circularized molecule by methods described in the parent application. The molecule designated pBG17 contains Ad5 sequences from bp 19 (left genomic end) to bp 341 with an artificially engineered BamH I restriction site inserted between approximately bp 188 and 189 in the Ad 5 sequences which is between "ITR" and the packaging signal, "Ψ", and known not to interfere with viral replication (Bett, A. J., W. Haddara, L. Prevec, and F. L. Graham. 1994, Proc. Natl. Acad. Sci USA 91: 8802–886). Ad5 sequences present in pBG17 then extend rightward of the packaging signal to approximately bp 341 at which position is located an Xba I restriction site followed by Ad 5 sequences from approximately bp 3534 to approximately bp 27864, then sequences comprising 1874 bp of DNA containing the pUC19 origin of replication and ampicillin resistance gene, and finally Ad5 bp 30996 to 35934 (right genomic end). By techniques that are readily employed by a person skilled in the art, lox P sites, which are well defined DNA sequences of about 34 bp, FRT sites, or other recombinase target recognition sites can be introduced into the Ad5 or other adenoviral genome at the Bam HI and XbaI sites flanking "Ψ". For example, synthetic double stranded oligodeoxynucleotides can be readily designed and synthesized such that they contain the lox P or FRT sequence recognized by Cre or FLP and are flanked by single stranded extensions that allow ligation into BamHI or XbaI cleaved DNA. Thus a person skilled in the art can readily obtain a plasmid such as that designated pBG17Lox1 (FIG. 4) having a lox P site introduced into the Bam HI site at nt 188, and subsequently pBG17Lox2 (FIG. 3) having an additional lox P site introduced into the XbaI site of PBG17Lox1. The plasmid pBG17 can be used to generate infectious virus by transfection of 293 cells. Equally, the plasmids pBG17Lox1 or pBG 17Lox2, will generate infectious virus (eg. AdBG17Lox2 illustrated in FIG. 3) since insertions of up to 271 bp can be engineered between the ITR and the packaging signal without interfering with viral replication and packaging of viral DNA (Hearing et al., Journal of Virology Vol. 61, p 2555, 1987). In the presence of Cre enzyme, the sequences containing the packaging signal are excised as a result of intramolecular recombination between the two lox P sites (FIG. 3, bottom) resulting in a viral genome that retains all the sequences necessary for replication but lacks the sequences needed for packaging of DNA into virions. Said genome may serve as a complementing viral genome to support the replication of a second virus, a vector, that lacks all or most of the viral genes necessary for viral replication as diagrammed in FIG. 2. These examples are not meant to be limiting as it will be appreciated that modified viruses similar in DNA structure to that of FIG. 3 can be generated by other means. For example a person skilled in the art could introduce lox P sites into other sites in the plasmids illustrated in FIG. 3 such as the Bst B1 or Pac I sites or into such other plasmids containing Ad sequences, or other Ad viral genomes as might be desirable. Use of Cre recombinase in this and other examples is not meant to be limiting as a person skilled in the art will readily appreciate, based on the instant disclosure, that other enzymes capable of catalyzing site specific recombination between DNA sequences recognized by said enzymes could equally be employed in place of the Cre recombinase. An example, not meant to be limiting, of such an enzyme that could be substituted for Cre is the "FLP" recombinase of yeast in combination with its target site (O'Gorman et al. Science 251, 1351, 1991).

As described herein and in prior applications from which this application claims priority with regard to the Cre/lox system, site specific recombination can be used to specifically excise the packaging signal from the DNA of an adenovirus (designated as a helper virus) in cells expressing Cre recombinase and infected with said helper virus. Because removal of the packaging signal does not interfere with viral DNA replication and transcription, said helper virus genome can undergo replication and can express viral proteins that allow for replication and encapsidation of DNA of a second virus, a vector (designated a helper dependent vector), that contains the inverted terminal repeat sequences and packaging signal which are the only viral DNA sequences required in cis for DNA replication and encapsidation. Thus, said helper dependent vector can have all or most of the viral coding sequences deleted and substituted with foreign DNA and said vector can be propagated in Cre expressing host cells coinfected with the said helper virus and the resulting vector preparations are substantially free of helper virus. The present patent disclosure demonstrates that the FLP recombinase, which recognizes a nucleic acid site known as FRT (O'Gorman, S., Fox, D. T. and Wahl, G. M. Recombinase-mediated gene activation and site specific integration in mammalian cell. Science 251: 1351–1355, 1991; Senecoff, J. F., Rossmeissl, P. J. and Cox, M. M., DNA recognition by the FLP recombinase of the yeast 2μ plasmid, J. Mol. Biol. 201: 405–491, 1988) may he used in similar fashion. It will be appreciated by those skilled in the art based on this disclosure that the method is not limited to the use of Cre recombinase and its recognition sites and FLP and its recognition sites, as other site specific recombinases that act in similar fashion to Cre and FLP could be substituted for Cre or FLP recombinases, or used in combination with such enzymes.

In particular, such other site specific recombinases that act in similar fashion to Cre and FLP are recognized in the art to be identified as recombinases belonging to the integrase family of recombinases (also referred to as the lambda, or λ, integrase family). Members of the integrase family of recombinases are recognized in the art to comprise a distinct class of structurally related proteins. For example, Kilby et al. (Trends in Genetics, 9:413–421, 1993) state that three site specific recombinases, "cre, FLP and R1 all belong to the λ integrase family of recombinases and show striking similarities, not only in the types of reaction they can carry out, but also in the structure of their target sites and mechanism of recombination (FIGS. 2,3)." Similarly, Kornberg & Baker (*DNA Replication*, Chapter 21–6, pp 806–817, W. H. Freeman, NY, 2$^{nd}$ Ed., 1992), after stating that "recombinases fall into two distinct class of structurally related proteins:," state that "the integrase family includes the P1 Cre and 2μ FLP proteins, λ Int protein, and several other phage integrases.[146] These proteins make staggered breaks in the DNA with 5' overhangs of 6 to 8 ntd and form a covalent DNA-protein linkage via a tyrosine to the 3'-P. They have in common a 40-amino-acid region near the C terminus in which histidine, arginine, and tyrosine residues, probably part of the active center, are completely conserved." The other class of structurally related recombinases according to Kornberg & Baker is the resolvase family.

Another embodiment of the invention provides human cells, such as 293 cells or other cells that may be deemed suitable in that they support the replication of the viral components of the invention, that express Cre, FLP or other recombinase and that can be transfected with the plasmids described herein to generate a helper virus from which the packaging signals have been removed through excision mediated by Cre, FLP or other recombinases. It will be appreciated by those skilled in the art that the requisite cell lines can be generated by transfecting 293 cells or other cells with a plasimd comprising the coding sequence for Cre, FLP or other recombinase under the control of suitable regulatory sequences including a promoter and polyadenylation signal and containing in addition a selectable gene encoding, for example, resistance to G418 or histidinol. Based on the instant disclosure, a person skilled in the art can readily obtain drug resistant cells that will express the Cre, FLP or other recombinase in addition to the drug resistance gene used for selection.

Figure 5:
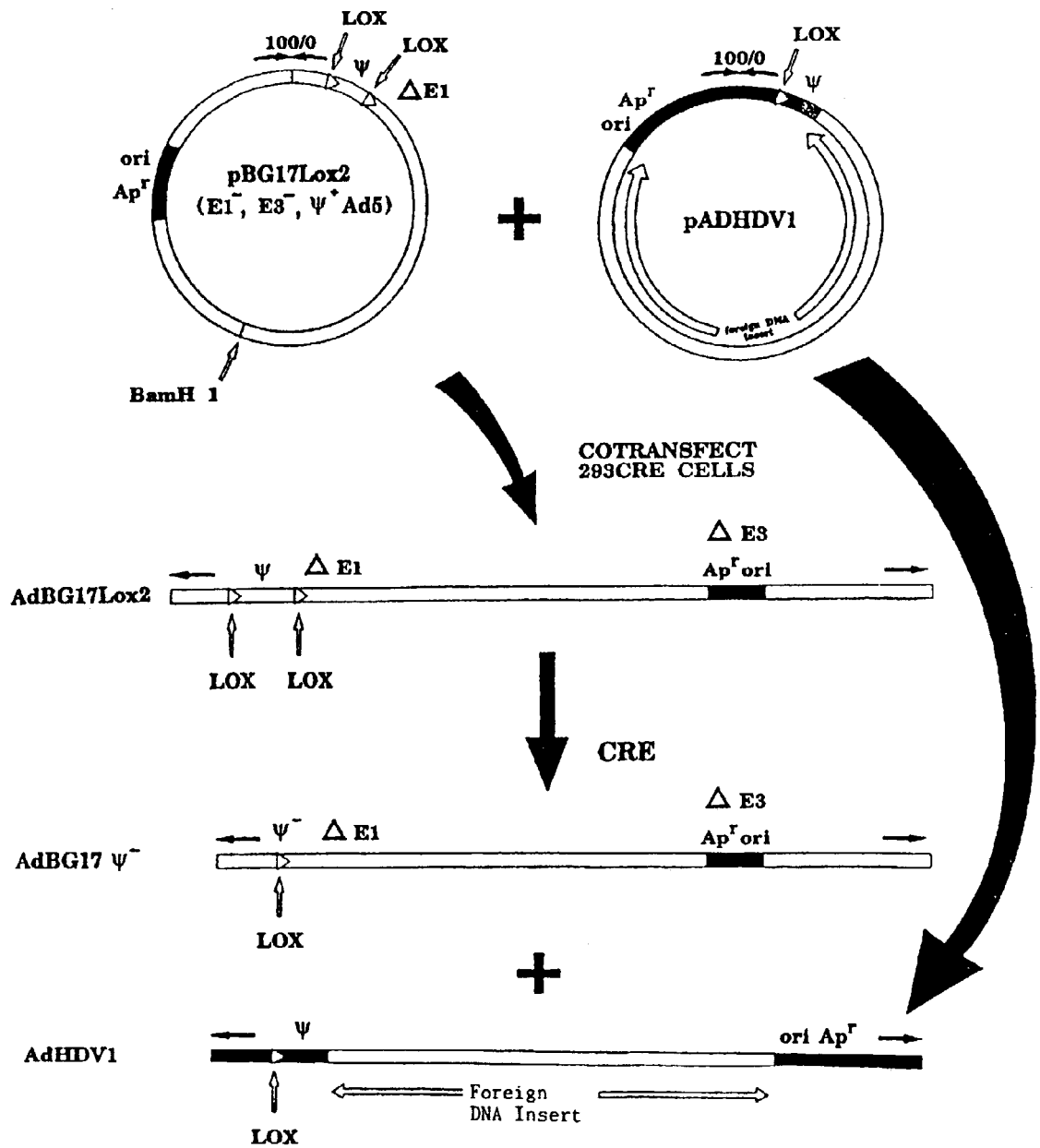
FIG. 5 is a diagrammatic representation of a means to obtain coreplicating helper and helper dependent viruses by cotransfection of 293Cre Cells.

In another embodiment of the invention, a plasmid consisting of sequences comprising the left ITR, the packaging signal, and the right ITR, and optionally containing additional viral sequences can be readily obtained. An example, which is not meant to be limiting, is illustrated in FIG. 4. In this example, pBG 17Lox1 DNA is digested with restriction enzymes XbaI and SmaI which cleave the viral DNA in pBG 17Lox1 at sites shown, as well as at other sites in viral DNA. The fragment containing the junction of viral termini (indicated by head to head arrows in FIG. 4) and the lox P site and packaging signal, can be purified and inserted into the polycloning site of a suitable cloning plasmid such as pUC18 or pUC19 to generate the plasmid designated as pPAD1. This example is not meant to be limiting as a person skilled in the art could equally insert said fragment into such other cloning plasmids as might be suitable or desirable. In the example illustrated, pPAD1 can serve as a vector for insertion of foreign DNA up to approximately 30 kb in size at one of the remaining restriction enzyme cloning sites present at the junctions of pUC and Ad5 DNA, to generate a plasmid such as pADHDV1, in which the open segment of pADHDV1 represents foreign DNA of arbitrary origin and sequence composition. The plasmid pADHDV1 contains all the Ad5 sequences needed in cis for viral DNA replication and packaging of viral DNA into virions. Provided that viral functions necessary in trans are supplied by a helper virus, therefore, pADHDV1 will have the potential to replicate as a helper dependent viral DNA molecule that will contain up to approximately 30–35 kb of foreign DNA flanked by viral DNA sequences from the left and right ends of the viral genome. It may be advantageous to include, as part of the foreign DNA inserted into pADHDV1, a DNA sequence capable of providing expression of a readily detectable reporter gene in addition to other sequences, the reporter gene providing a simple means of identifying cells or groups of cells that are infected with the virus ADHDV1 derived from pADHDV1. As an example, which is not meant to be limiting, a person skilled in the art could include in pADHDV1, sequences coding for bacterial β-galactosidase, expression of which is readily detectable by exposure of cells to X-gal. Furthermore, in the example shown in FIG. 4, pPAD1 and pADHDV1 contain a single lox P site at Ad5 nt 189, that is at the same site as for one of the lox P insertions in pBG17Lox 1&2. Although this example is not meant to be limiting, placement of a lox P site at this position in pPAD1, pADHDV1, and derivatives, may serve to reduce the efficiency of recombination between helper virus and vector during coreplication of the two viruses as illustrated in FIGS. 2 and 5. However, one skilled in the art will recognize, based on the instant disclosure, that placement of a loxP site in pPAD1 or like plasmid is not an essential feature of the system, as we have found that systems without a lox site at nt 189 operate well. Like strategies may be employed when using FLP/FRT or other site-specific recombinase systems.

In another embodiment of the invention, coreplication of helper virus comprising sequences derived from a plasmid such as pBG17Lox2 and a helper dependent virus comprising sequences derived from a plasmid such as pADHDV1 may be achieved by cotransfection of cells with said plasmids to generate replicating viral genomes. In the example illustrated in FIG. 5, which is not meant to be limiting, AdBG17Lox2 will, in the presence of Cre recombinase, be converted to AdBG174$_\Psi$-, by excision of the sequences bracketed by lox P sites. The virus AdBG17$_\Psi$- will, by virtue of the removal of the packaging signals, be unable to package its genome into virions but will be able to replicate its DNA and provide viral functions necessary in trains for viral replication and thereby provide complementing functions for replication of the helper dependent virus, AdHDV1. Because AdHDV1 retains the packaging signals, the DNA of this helper dependent virus will be packaged into virions. The helper dependent virus AdHDV1 may be recovered, and optionally purified and concentrated by isopycnic centrifugation in CsCl gradients to produce helper dependent virus preparations substantially free or totally free of contaminating helper virus. Substantially identical methodology may be employed when using FLP/FRT or other site-specific recombinase systems.

In another embodiment of tie invention 293 cells or other human cells that do not express Cre, FLP or other recombinases, may be transfected with a plasmid. Such as that designated as pBG17Lox2 in FIGS. 3 and 5, or other equivalents thereof using relevant recombinase target recognition sites, such as FRT, to produce a virus such as that designated as AdBG17Lox2. Said virus may replicate in said cells without undergoing excision of sequences bracketed by lox P and can therefore be readily propagated. Coinfection of 293Cre or equivalent cells with AdBG17Lox2 and AdHDV1 will lead to formation of AdBG17$_\Psi$- which will complement the growth of AdHDV1 resulting in coreplication of both viral genomes but packaging only of AdHDV1 DNA into viral particles.

Having generally described this invention, as disclosed and claimed herein, the following specific exemplary support is provided to demonstrate the functionality of the disclosed and claimed system both in vitro and in vivo. However, this invention should not be interpreted as being limited to the specifics of the following examples. Rather, the scope of this invention should be determined through consultation of the claims appended hereto and equivalents thereof.

EXAMPLE 1

An Adenoviral Vector Deleted for all Viral Coding Sequences Results in Enhanced Safety and Extended Expression of a Leptin Transgene Experimental Synopsis and Conclusions Drawn:

Adenoviral (Ad) mediated in vivo gene transfer and expression are limited in part by cellular immune responses to viral-encoded proteins and/or transgene immunogenicity. In an attempt to diminish the former responses, we have previously developed and described helper-dependent (HD) Ad vectors in which the viral protein coding sequences are completely eliminated. These HD vectors have up to 37 kb insert capacity, are easily propagated in a Cre recombinase-based system, and can be produced to high concentration and purity (>99.9% helper-free vector). In this study, we compared safety and efficacy of leptin gene delivery mediated by an HD vector (HD-leptin) and a first-generation E1-deleted Ad vector (Ad-leptin) in normal lean and ob/ob (leptin-deficient) mice. In contrast to evidence of liver toxicity, inflammation, and cellular infiltration observed with Ad-leptin delivery in mice, HD-leptin delivery was associated with a significant improvement in associated safety/toxicity and resulted in efficient gene delivery, prolonged elevation of serum leptin levels, and associated weight loss. The greater safety, efficient gene delivery, and increased insert capacity of HD vectors are significant improvements over current Ad vectors and represent favorable features especially for clinical gene therapy applications.

Background for this Example:

Adenoviral (Ad) vectors are currently among the most efficient gene transfer vehicles for both in vitro and in vivo delivery, but the utilization of current Ad vectors for many gene therapy applications is limited by the transient nature of transgene expression obtained by these vectors (Stratford-Perricaudet, L. D., Levrero, M., Chasse, J., Perricaudet, M. & Briand, P. (1990) Hum. Gene Ther. 1, 241–256.; Kay, M. A., Li, Q., Liu, R. J.-J., Leland, F., Roman C., Finegold, M. & Woo, S. L. C. (1992) Hum. Gene Ther. 3, 641–647.; Herz, J. & Gerard, R. D. (1993) Proc. Natl. Acad. Sci. USA 90, 2812–2816.; Englehardt, J. F., Simon, R. H., Yang, Y., Zepeda, M., Wber-Pendleton, S., Doranz, B., Grossman, M & Wilson, J. M. (1993) Hum. Gene Ther. 4, 757–769.; Morsy, M. A., Alford, E. L., Bett, A., Graham, F. L. & Caskey, C. T. (1993) J. Clin. Invest. 92, 1580–1586.; Morsy, M. A., Zhao, J. Z., Warman, A. W., O'Brien, W. E., Graham, F. L. & Caskey, C. T. (1996) J. Clin. Invest. 97, 826–832.; Muzzin, P., Eisensmith, R. C., Copeland, K. C. & Woo, S. L. C. (1996) Proc. Natl. Acad. Sci. USA 93, 14804–14808). Several factors have been shown to contribute to and modulate the duration of Ad-mediated gene expression and the immunogenicity of these vectors, including "leaky" viral protein expression and the transgene that is delivered (Yang, Y., Nunes, F. A., Berencsi, K., Furth, E. E., Gonczol, E. & Wilson, J. M. (1994) Proc. Natl. Acad. Sci. USA 91, 4407–4411.; Yang, Y., Ertl, H. D. & Wilson, J. M. (1995)J. Virol. 69, 2004–2015.; Lochmuller, H., Petrof, B. J., Pari, G., Larochelle, N., Dodelet, V., Wang, Q., Allen, C., Prescott, S., Massie, B., Nalbantoglu, J., et al. (1996) Gene Ther. 3, 706–716.; Gahery-Segard H., Juilliard, V., Gaston, J., Lengagne, R., Pavirani, A., Boulanger, P. & Guillet, J. G. (1997) Eur. J. Immunol 27, 653–659.; Kajiwara, K., Byrnes, A. P., Charlton, H. M., Wood, M. J. & Wood, K. J., (1997) Hum Gene Ther. 8, 45–56.; Kaplan, J. M., Armentano, D., Sparer, T. E., Wynn, S. G., Peterson, P. A., Wadsworth, S. C., Couture, K. K, Pennington, S. E., St. George, J. A., Gooding, L. R. & Smith, A. E. (1997) Hum. Gene Ther 8, 45–46.; Worgall, S., Wolff, G., Falck-Pedersen, E. & Crystal, R. G. (1997) Hum. Gene Ther. 8, 37–44.; Tripathy, S. K., Black, H. B., Goldwasser, E. & Lieden, J. M. (1996) Natl. Med. 2, 545–550.). The development of Ad vectors that are deleted in all viral protein-coding sequences offers the prospect of a potentially safer, less immunogenic vector with an insert capacity of up to 37 kb (Mitani, K., Graham, F. L., Caskey, C. T. & Kochanek, S., (1995) *Proc. Natl. Acad. Sci.* USA 92, 3854–3858.; Kochanek, S., Clemens, P. R., Mitani, K., Chen, H. H., Campbell, K. P. & Caskey, C. T. (1996) *Proc. Natl. Acad. Sci.* USA 93, 5731–5736.; Clemens, P. R., Kochaneck, S., Sunada, Y., Chan, S., Chen, H. H., Campbell, K. P. & Caskey, C. T. (1996) *Gene Ther.* 3, 965–72.; Chen, H. H., Mack, L. M., Kelly, R., Ontell, M., Kochaniek, S. & Clemens, P. R. (1997) *Proc. Natl. Acad. Sci.* USA 94, 965–972.; Fisher, K. J., Choi, H., Burda, J., Chen, S. & Wilson, J. M. (1996) *Virology* 217, 11–22.; Kumar-Singh, R. & Chamberlain, J. S. (1996) *Hum. Mol. Gent.* 5, 913–921.; Hardy, S., Kitamura, M., Harris-Stansil, T., Dai, Y. & Phipps, M. L. (1997) *J. Virol.* 71, 1842–1849.; Lieber, A., He, C., Kirillova, I. & Kay, M. A. (1996) *J. Virol.* 70 8944–8960; Parks, R. J., Chen L., Anton, M., Sankar, U., Rudnicki, M. A. & Graham, F. L. (1996) *Proc. Natl. Acad. Sci.* USA 93, 13565–13570; Haecker, S. E., Stedman, H. H., Balice-Gordon, R. J., Smith, D. B., Greelish, J. P., Mitchell, M. A., Wells, A., Sweeney, H. L. & Wilson, J. M. (1996) *Hum. Gen. Ther.* 7, 1907–1914; Schiedner, G., Morral, N., Parks, R. J., Wu, Y., Koopmans, S. C., Langston, C., Graham, F. L., Beaudet, A. L. & Kochanek, S. (1998) *Natl. Genet.* 18, 180–183.). This vector is supplied in trans with the structural proteins required for packaging and rescue and is thus helper-dependent (HD) (Parks, R. J., Chen L., Anton, M., Sankar, U., Rudnicki, M. A. & Graham, F. L. (1996) *Proc. Natl. Acad. Sci.* USA 93, 13565–13570).

Leptin has been recently identified as a potent modulator of weight and food intake. Daily delivery of recombinant leptin protein was shown to induce weight reduction, supress appetite, and decrease blood insulin and glucose levels in ob/ob (leptin-deficient) mice (Halaas, J. L., Gajiwala, K. S., Maffei, M., Cohen, S. L., Chait, B. T., Rabinowitz, D., Lallone, R. L., Burley, S. K. & Friedman, J. M. (1995) *Science* 269, 543–546; Pellymouter, M. A., Cullen, M. J., Hecht, R., Winters, D., Boone, T. & Collins, F. (1995) *Science* 269, 546–549; Campfield, L. A., Smith, F. J., Guisez, Y., Devos, R. & Burn, P. (1995) *Science* 269, 546–549.). It has been shown that delivery of the leptin cDNA by first-generation Ad vectors (Ad-leptin) may substitute for daily recombinant leptin protein treatment, although the effects were transient in both lean and ob/ob treated mice (Muzzin, P., Eisensmith, R. C., Copeland, K. C. & Woo, S. L. C. (1996) *Proc. Natl. Acad. Sci.* USA 93, 14804–14808; Morsy, M. A., Gu, M., Zhao, J. Z., Holder, D. J., Rogers, I. T., Pouch, W., Motzel, S. L., Klein, H. J., Gupta, S. K., Liang, X., et al. (1998) *Gene Ther.* 5, 8–18.). In the present study, we delivered the leptin cDNA using the HD virus (HD-leptin), testing the hypothesis that elimination of the viral protein coding sequences would diminish the vector's cellular immunogenicity and toxicity, and hence support its longevity in vivo. Because both the viral proteins and the transgene were factors implicated in the cellular immunogenicity of recombinant Ad viruses, we designed experiments to compare the HD and Ad vectors in ob/ob mice that are naive to leptin (in which the protein is potentially immunogenic), as well as in lean mice that normally express leptin.

In this study, we show that HD-leptin provided greater safety as reflected by absence of liver toxicity, cellular infiltrates, extended longevity of gene-expression, and stability of vector DNA in livers of treated mice over that observed with Ad-leptin treatment.

Materials and Methods

Construction of Vectors.

Construction of Ad-leptin and Ad-β-galalactosidase (β-gal) recombinant vectors has been described (Morsy, M. A., Gu, M., Zhao, J. Z., Holder, D. J., Rogers, I. T., Pouch, W., Motzel, S. L., Klein, H. J., Gupta, S. K., Liang, X., et al. (1998) *Gene Ther.* 5, 8–18.). The expression cassettes contain the human cytomegalovirus (HCMV) promoter (Invitrogen), the transgene, and the bovine growth hormone poly(A) sequence. First generation vectors were propagated and titered as described (Graham, F. L., Smiley, J., Russell, W. C. & Nairn, R. (1977) *J. Gen. Virol.* 36, 59–72; Graham, F. L. & Prevec, L. (1991) in *Gene Transfer and Expression Protocols.*, ed. Murray, E. J. (Humana, Clinton, N.J.), pp. 109–128.). The HD vector constructed for this study (HD-leptin) was prepared by releasing the lineal backbone structure of HD-leptin from its plasmid pΔSTK120-HCMV-mOb-BGHpA (by PmeI digest) and transfecting the linear DNA into 293-cre4 cells followed by helper infection as described in HD-leptin propagation section below. Two different structures were used for rescuing HD viruses expressing leptin, HD-leptin (used in all the in vivo studies reported in this article), and HD-leptin-monomer. The structure of the HD-leptin plasmid is a pBluescript HKS based plasmid that contains (in the following order) the Ad5 inverted terminal repeat (ITR) sequences and the packaging signal $\psi$, 440 bp, (nucleotides 1–440): a 5,072-bp fragment of hypoxanthine guanine phosphoribosyltransferase (nucleotides 12,373–17,781 in gb:humhprtb); the leptin expression cassette, 1,835 bp; a HindIII 9,063-bp fragment of C346 cosmid (nucleotides 12,421–21,484 in gb:L31948); and the right-end terminus of Ad5, composed of the ITR sequence, 117 bp (nucleotides 35,818–35,935); with the intervening multiple cloning sites between junctions of the different fragments the total size is 19.6 kb including 2.9 kb of the pBluescript HKS. The 2.9 kb of pBluescript HKS is eliminated before HD vector rescue by linearizing the plasmid with two PmeI flanking sites. HD-leptin-monomer plasmid (pSTK120-HCMV-mOb-BGHpA) differs in that the hypoxanthine guanine phosphoribosyltransferase "stuffer" is a larger fragment of 16,054 bp (nucleotides 1,799–17,853 in gb:humhprtb), total size ≈30 kb including 2.9 kb of the pBluescript HKS, which as in the case of HD-leptin plasmid, is also eliminated by linearizing the plasmid with two PmeI flanking sites and releasing the HD-leptin-monomer fragment.

Propagation of the HD Viruses.

For propagation of the HD viruses, we used a helper virus system consisting of a modified first-generation E1-deleted vector with lox sites flanking the packaging signals (AdLC8clucl), and a 293 cell line derivative expressing Cre recombinase (293-cre4)(Parks, R. J., Chen, L., Anton, M., Sankar, U., Rudnicki, M. A. & Graham, F. L. (1996) *Proc. Natl. Acad. Sci.* USA 93, 13565–13570; Chen, L., Anton, M. & Graham, F. L. (1996) *Som. Cell Mol. Genet.* 22, 477–488.). HD-leptin vector DNA was excised from the plasmid backbone (by PmeI digestion) and 4 μg were used to transfect semiconfluent 293-cre4 cells in 6-cm plates. After an overnight incubation, cells were infected at a multiplicity of infection of 1 with the helper virus AdLC8clucl. Cells were monitored for complete cytopathic effect, at which point cells were collected and lysate was used for serial propagation and expansion viral stock by slight modification over what was described (Parks, R. J., Chen, L., Anton, M., Sankar, U., Rudnicki, M. A. & Graham, F. L. (1996) *Proc. Natl. Acad. Sci.* USA 93, 13565–13570;

Parks, R. J. & Graham, F. L. (1997) *J. Virol.* 71, 3293–3298.). Two ml of lysate collected from P1 (transfection/infection step) was used to infect 6-cm plates of semiconfluent 293-cre4 for 24 hours, supplemented with 1 ml of fresh medium. After the 24–1 hr incubation, the helper virus AdLC8clucl was added at a multiplicity of infection of 1, to the cells. P2 lysate was collected upon detection of cytopathic effect. The same procedure was repeated for another three propagation's (P3, P4, and P5) infecting 10-cm plates followed by 15-cm plates of semiconfluent 293-cre4 cells, respectively. Lysate collected from P4 was used to infect twenty 15-cm plates (1 ml of lysate added to 24 ml of fresh medium), and again upon detection of cytopathic effect the lysate was collected and cesium chloride banded as described (Graham, F. L. & Prevec, L. (1991) in *Gene Transfer and Expression Protocols*., ed. Murray, E. J. (Humana, Clinton, N.J.), pp. 109–128.). The banded viruses were analyzed by restriction mapping and the HD-leptin virus was sequenced for verification of structure.

The final stock of HD-leptin was harvested from $\approx 1.2 \times 10^9$ 293-cre4 cells and the cesium chloride banded viral stock yield was $\approx 8 \times 10^{12}$ particles ($2 \times 10^{12}$/ml). The helper virus (AdLC8clucl) content in the HD-leptin stock was $1.5 \times 10^7$ plaque-forming units per ml. Fifty microliters ($1-2 \times 10^{11}$ OD particles per dose, containing $\approx 7.5 \times 10^5$ plaque-forming units helper, i.e., <0.1% contamination with helper per estimated infectious HD dose) of the stock were diluted with dialysis buffer to 100 μl for the mouse tail vein injections.

Repeat of HD-Leptin Viral Rescue.

Three independent rescues of the HD-leptin recombinant virus, initiated at the first step (P1), which is the transfection of pΔSTK120-HCMV-mOb-BGHpA resulted in an identical, and stable structure of HD-leptin. Seven different enzymes were used for verifying the structures of the recombinant HD viruses; Asp-718, EagI, FseI, HindIII, PacI, SmaI, and XhoI. Digested viral DNA (50–100 ng) was analyzed by Southern blot analysis, 1fragments were radio labeled using T4 DNA poymerase, DNA fragments were viewed on a 1.0 or 0.5% (for sizing purposes in case of undigested DNA extracted from HD-leptin and Ad-leptin) agarose gels in Tris/acetate/EDTA (TAE) buffer, and identified by radioautography or ethidium bromide staining.

PCR Amplification of the Junction Fragment and Sequencing.

A primer flanking the junction fragment was used for PCR, primer J4-F:5'-CTCTTCTTCTGTCACACCCCTC-CCUC-3' (SEQ ID NO:1) was used individually to amplify the junction-fragment of HD-leptin, the fragment generated was ~300 bp, and was cloned into PCR 2.1 vector (Invitrogen) and sequenced.

Mouse Colony.

ob/ob (C57BL/J6-ob/ob) mice and homozygous normal lean (C57BL/J6) litter mates (age-matched females), were purchased from The Jackson Laboratory for use in this study. Animals were free of all common murine pathogens. Eight-to twelve-week-old mice (ob/ob $\approx 70$ g and lean $\approx 28$ g) were redistributed based on equal representation of weight and caged in groups of five on day 0, immediately preceding treatment. After a series of baseline blood samples were obtained by tail incision from conscious mice, animals were divided into four groups and received by tail vein injection a single 100-μl aliquot containing $1-2 \times 10^{11}$ particles of HD-leptin, Ad-leptin, Ad-β-gal (control), or dialysis buffer (control). Body weight and food intake were measured daily, and blood was collected 2–3 times weekly, pre- and post-treatment.

Animals were killed by carbon dioxide inhalation and organs removed for immunohistochemistry and RNA analysis. All animals used in this study were maintained in accordance with the "Guide for the Care and Use of Laboratory Animals" (Institute for Laboratory Animal Resources, National Research Council, 1996). The protocol was approved by the Institutional Animal Care and Use Committee, Merck.

Histopathology Studies.

Mice (n=3 per treatment per time point) were humanely killed, and liver samples were collected and fixed in 10% buffered formalin. Tissues were routinely processed through paraffin, sectioned at 5 microns, and stained with hematoxylin and eosin. Replicate unstained slides also were prepared using standard procedures for immunohistochemistry and stained for the presence of CD3 (T cell) and CD45R (B cell) determinants on infiltrating or intrinsic cells (not shown).

Blood Measurements.

Blood samples were obtained by tail incision and collected into heparinized microhematocrit tubes (VWR Scientific) every 2–3 days during the course of the study. Tubes were centrifuged at 13,700×g for 2 min, and hematocrit values were monitored. Plasma was collected for measurement of aspartate, aminotransferase (AST), alanine aminotransferase (ALT), leptin, glucose, and insulin levels. ALT and AST were measured using ALT/serum glutamic oxaloacetic transaminase and AST/serum glutamic pyruvic transaminase, DT slides, respectively (Vitros Chemistry Products, Johnson & Johnson). Leptin and insulin levels were measured by radioimmunoassay performed by Linco Research Immunoassay (St. Charles, Mo.). Glucose levels were measured using Kodak Ektachem DT slides (Eastman Kodak).

Northern and Southern Blot Analysis.

For Northern blot analysis, total RNA was extracted (Trizol, GIBCO) from livers of Ad-leptin-treated and HD-leptin-treated mice at 1-, 2-, 4-, and 8-week intervals, and untreated mice. Leptin RNA message was detected by Northern blot analysis (Maniatis, T., Fritsch, E. F. & Sambrook, J. (1982) *Molecular Cloning: A Laboratory Manual* (Cold Spring Harbor Lab. Press, Plainview, N.Y.) using leptin cDNA as a probe that recognizes a single $\approx 500$ bp band (Morsy, M. A., Gu, M., Zhao, J. Z., Holder, D. J., Rogers, I. T., Pouch, W., Motzel, S. L., Klein, H. J., Gupta, S. K., Liang, X., et al. (1998) *Gene Ther.* 5, 8–18.). A probe for β-actin was used as the internal control ($\approx 1$ kb) (Biochain, San Leandro, Calif.). Southern blot analysis (Maniatis, T., Fritsch, E. F. & Sambrook, J. (1982) *Molecular Cloning: A Laboratory Manual* (Cold Spring Harbor Lab. Press, Plainview, N.Y.) was used to investigate the stability of vector DNA. Genomic DNA was extracted from livers (pooled DNA, n=3 per treatment per time point) of ob/ob and lean mice were treated with Ad-β-gal, Ad-leptin or HD-leptin. Control animals were injected with similar volumes of dialysis buffer. Pooled (n=3) genomic DNA was digested with HindIII restriction enzyme, and 20 μg of digested DNA were loaded on 0.8% TAE agarose gels. For copy number estimation, 20 μg control DNA were spiked with HD vector DNA equivalent to 2.0, 1.0, 0.2, and 0.1 copies per cell, and the mixture digested with HindIII restriction enzyme followed by Southern blot analysis. The filters were hybridized with a mouse leptin cDNA ($\approx 500$ bp) probe, which hybridized to a single HindIII fragment containing the leptin insert in both the HD-leptin ($\approx 6$ kb), and Ad-leptin ($\approx 1.2$ kb) vectors. Developed autoradiographs were scanned (Personal Densitometer SI, Molecular Dynamics) and the relative band densities quantitated (IMAGE QUANT software, Molecular Dynamics). To normalize DNA concentration and to estimate relative vector DNA stability between treatment time points, a detected internal leptin genomic DNA signal was used as control. Copy number equivalence were assigned based on comparisons to the relative density ratio between the internal genomic signal and the leptin signal of spiked vector DNA in a copy number control experiment.

Results and Discussion

Figure 6:
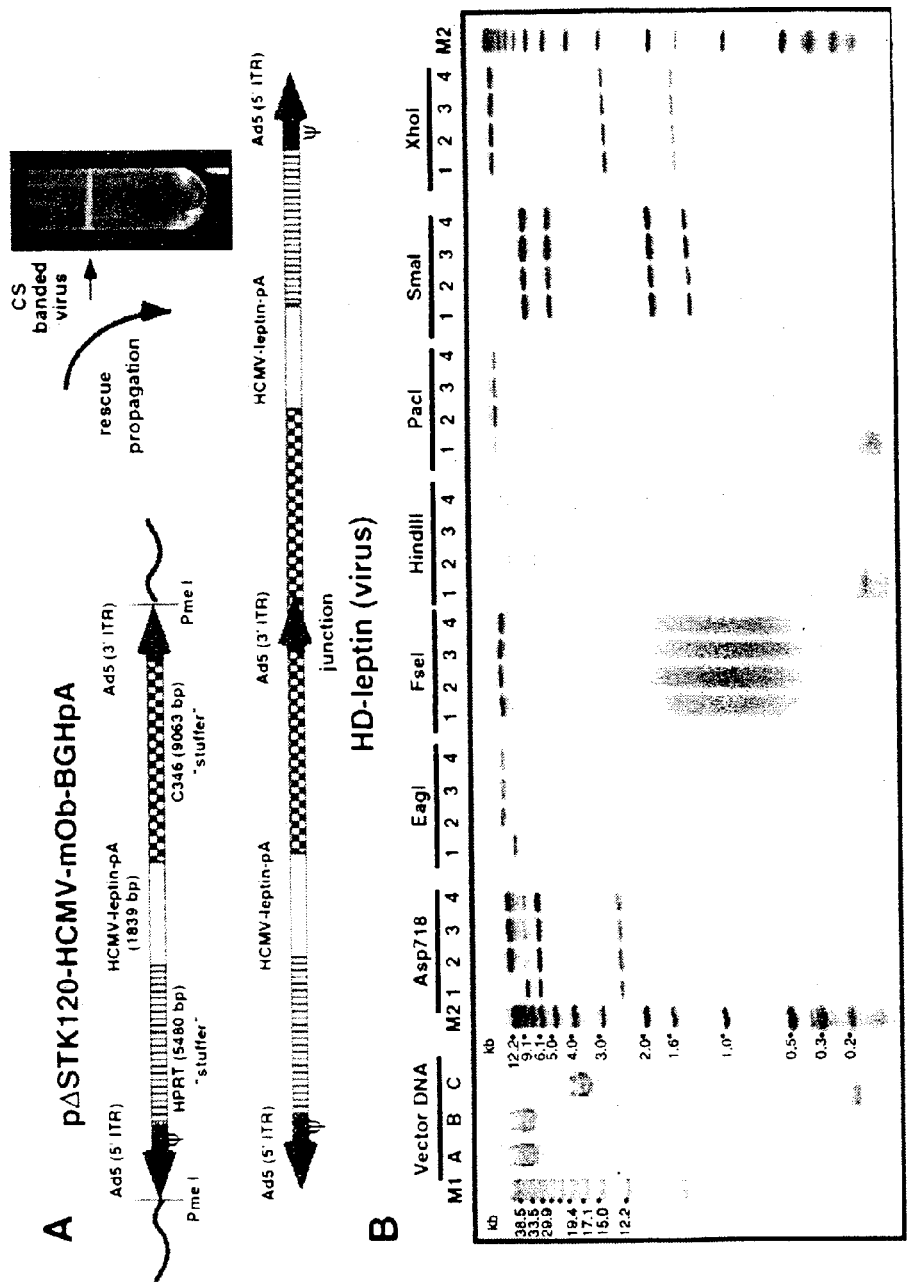
FIG. 6. Shows an HD leptin construct. (A) The DNA composite fragments of pΔSTK120-HCMV-mOb-BGHpA (≈19.6 kb total size) are from left to right: the left end terminus of Ad5, composed of the ITR sequences and the packaging signal Ψ (nucleotides 1–440, solid arrow); the 5,072-bp fragment of hypoxanthine guanine phophoribosyltransferase (HPRT) (nucleotides 12,373–17,853 in gb:humhprtb, striped area); the leptin expression cassette (1,835 bp), composed of the HCMV promoter, the murine leptin cDNA (500 bp) and the bovine growth hormone poly(A) tail (open area) (inserted in the complementary orientation): the HindIII 9063-bp fragment of C346 cosmid (nucleotides 12,421–21,484 in gb:L31948, checkered area); and the right end terminus of Ad5, composed of the ITR sequence (nucleotides 35,818–35,935). The ITRs are flanked by unique PmeI restriction sites used to liberate the vector fragment from the plasmid backbone before the initial transfection into 293-cre4 cells for viral rescue and propagation (released fragment is 16.7 kb). To the right of the vector structures is a representative cesuim chloride banded HD-leptin vector stock, at the final stage of band collection. The band is single, compact, and thick. (B) The structure and tail-to-tail concatamerizations (junction is at the 3' ITR ends of ΔSTK120-HCMV-mOb-BGHpA), is verified by the restriction enzyme pattern of the three independently rescued viruses. The gel, labeled Vector DNA, shows 0.5 μg of DNA extracted from the HD-leptin viral stock (lane A), Ad-leptin stock (lane B) and the PmeI cut pΔSTK120-HCMV-mOb-BGHpA (lane C) compared on a 0.5% agarose gel for sizing. Both HD-leptin (33 kb) and Ad-leptin (34 kb) extracted DNA migrate, as expected, between 38.5–29.9 kb, and the cut ΔSTK120-HCMV-mOb-BGHpA (16.7 kb) migrates between 17.1 and 15.0 kb, the smaller band corresponds to the plasmid backbone (2.9 kb), and the faint band in lane A represents the trace amount of the propagated 16.7-kb linearized vector. Structures ΔSTK120-HCMV-mOb-BGHpA (lane 1) (gel extracted after separation of plasmid and backbone by PmeI digestion) and the three HD-leptin vectors (lanes 2–4) are compared by restriction analysis. The expected fragment sizes for HD-leptin are: for Asp-718: 15,391-single band(s), 6,296-double band(d), and 2,501-d; EagI:20,455-s 1,715-s and 6,270/6,266-d; FseI: 16,523/16, 458-d; HindIII: 10,207/10,174-d, 5845-d, and 454/450-d; PacI: 16,516/16,465-d; SmaI: 6,701-d, 5,163-d, 2,180-d, 1,715-s, and 1,589-d, and XhoI: 11,833-d, 2,964/2,953-d; and 1,701/1,697-d bp. The expected fragment sizes for ΔSTK120-HCMV-mOb-BGHpA are: for Asp-718: 7,837-s, 6,296-s, and 2,501-s; EagI: 10,364-s and 6,266-s; FseI: 16,458-s and 172-s; HindIII: 10,174-s, 5848-s, 450-s, and 158-s; PacI: 16,465-s and 165-s; SmaI: 6,701-s, 5,163-s, 2,180-s, 1,589-s and 997-s, and XhoI: 11833-s, 2964-s, 1697-s and 136-s bp. M1 and M2 are DNA markers (8–48 kb, Bio-Rad, and 1-kb DNA ladder, GIBCO/Life Technologies, Gaithersburg, Md., respectively).]

The HD viruses rescued and propagated were analyzed both for structure verification and for helper-load contamination. HD-leptin (used in this study) was generated from a 16.7-kb vector fragment (FIG. 6). This fragment when transfected and propagated in the presence of a helper virus resulted in an HD-virus with a full length of ≈33 kb (FIG. 6). The full-length structure is a tail-to-tail concatamerization recombinant virus (FIG. 6A). This virus has several interesting characteristics. (i) The HD-leptin structure contains a duplicated 5'ITR and packaging signal sequence, one copy at each end of the recombinant virus (FIG. 6A). (ii) This structure is very stable throughout multiple propagations (originating from viral stock). In addition, repeated rescue (originating from the 16.7-kb DNA fragment) results in a single concatamerization species (FIG. 6B). The three HD-leptin recombinant viruses shown, are all independent results of a tail to tail (3' ITR—3' ITR) concatamerization of two ΔSTK120-HCMV-mOb-BGHpA molecules. The HD-leptin structure contains two copies of the 5'ITR and packaging signals that flank the recombinant virus at both ends and the 3'ITR (one copy only) at the junction of the two molecules. No other concatamerization species were identified in any of the three independent rescues (by restriction mapping and analysis of radiolabeled digestion fragments). (iii) The helper virus contamination load is consistently very low; <0.1%/infectious HD unit; <1 plaque-forming unit of helper virus per 100,000 OD particles per ml of HD stock (minimum estimated HD infectious unit: OD particle is 1:100). HD-leptin expressed leptin at levels comparable to its counterpart first generation Ad-leptin (data not shown).

In contrast, the HD-leptin monomer, containing a single copy of the packaging signal sequence at the left arm only, consistently results in at least 3–10 fold higher load of helper virus contamination (1 plaque-forming unit of helper virus per $10^3$–$10^4$ OD particles per ml) in HD-leptin monomer stock. Given that all the various viral stocks were prepared following the same standard laboratory procedures, the consistently lower levels of helper contamination in the concatamerized HD-leptin viral stock may be attributed to either the duplicated copy of packaging signal sequence or the differences in backbone composition, possibilities now under investigation.

Figure 7:
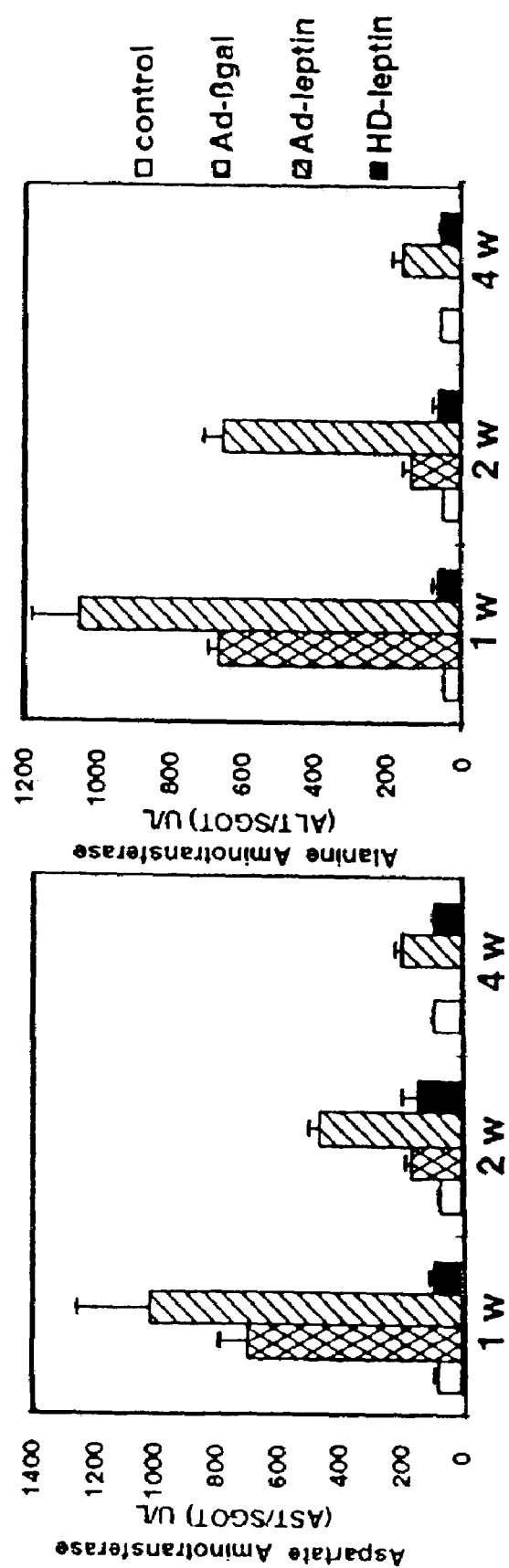
FIG. 7 shows results of AST and ALT assays for mice which were treated with Ad-β-gal, Ad-leptin, and HD-leptin or dialysis buffer (controls). AST and ALT levels in the sera of lean control and treated mice are plotted at 1, 2, and 4 weeks posttreatment.

As a first measure of the difference between first generation Ad and HD vectors, safety studies were conducted in control and treated lean and ob/ob mice. Mice were treated with a single tail intravenous infusion of 1–2×$10^{11}$ particles of either HD-leptin, Ad-leptin, control Ad-β-gal vector or an equal volume of dialysis buffer. FIG. 7 shows the levels of AST and ALT in the sera of lean mice at one, two and four weeks posttreatment (similar results were observed in treated ob/ob mice; data not shown). Liver toxicity, as reflected by the significant elevation in AST and ALT serum levels over basal control levels, was observed only in mice treated with Ad-β-gal and Ad-leptin, but not HD-leptin. Ad-vector-associated toxicity observed in both the lean and ob/ob treated mice was most significant at one week, was present but to a less significant extent at two weeks, and was resolved by 4 weeks posttreatment. In contrast, HD-treatment was not associated with liver toxicity as reflected by the AST and ALT serum levels that were essentially indistinguishable from controls.

Figure 8:
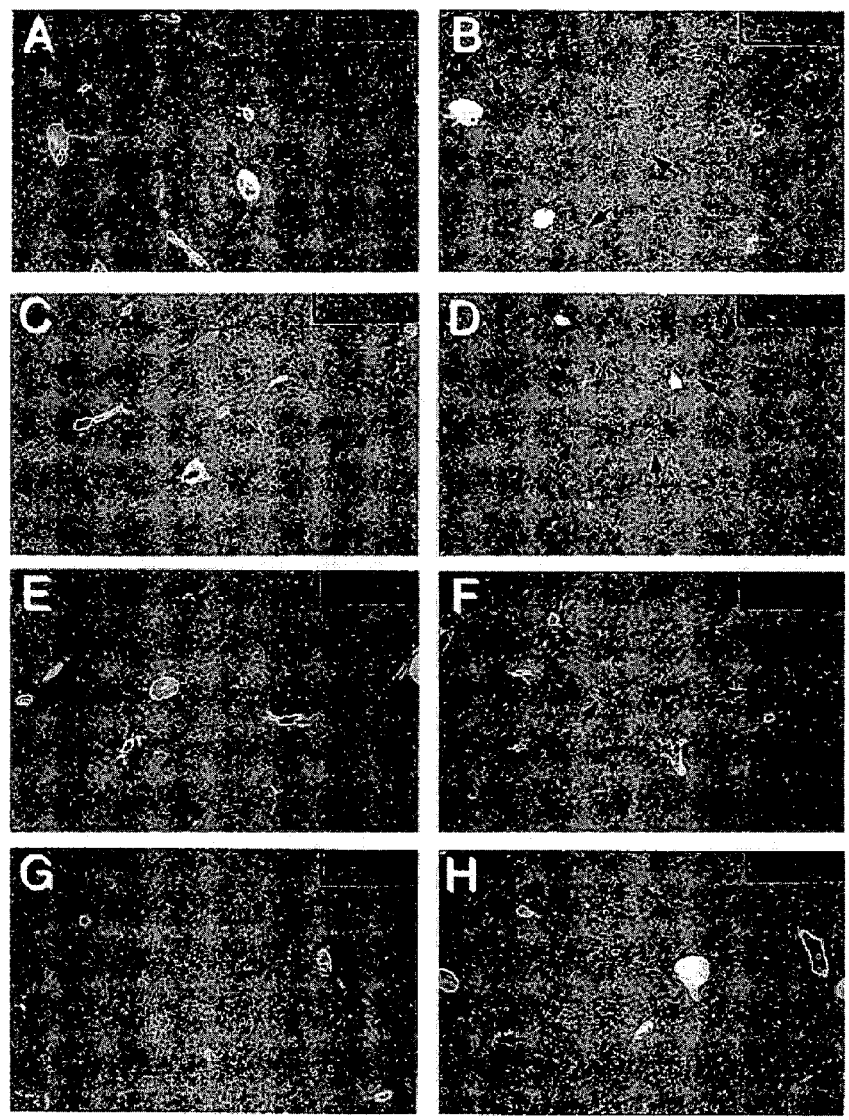
FIG. 8 shows photomicrographs illustrating liver histopathology in lean mice. (A) Untreated control lean. (B) Positive Ad-β gal-treated control lean, 1 week posttreatment. (C) HD-leptin-treated lean, 1 week posttreatment. (D) Ad-leptin-treated lean, 1 week posttreatment. (E) HD-leptin-treated lean, 2 weeks posttreatment. (F) Ad-leptin-treated lean, 2 weeks posttreatment. (G) HD-leptin-treated lean, 4 weeks posttreatment. (H) Ad-leptin-treated lean, 4 weeks posttreatment. (Bar=100 μM.)

Liver sections of HD-leptin-treated lean mice (FIG. 8) were histologically indistinguishable from control liver sections (FIG. 8A) at all timepoints tested posttreatment [1(FIG. 8C), 2(FIG. 8E), and 4(FIG. 8G) weeks). Occasional perivascular clusters of 50:50 T and B cells and small foci of cellular infiltrates in HD-leptin-treated as well as in untreated control mice were observed. In contrast, Ad-leptin and Ad-β-gal treated mice displayed hepatic pathology throughout the posttreatment intervals. At 1 week posttreatment, both Ad-β-gal (FIG. 8B) and Ad-leptin-treated (FIG. 8D) mice display degenerative hepatic pathology characterized by foci of round cell infiltration (solid arrows) composed almost entirely (>98%) of T-cells (data not shown), individual liver cell necrosis, increased liver cell mitotic activity, and dissociation of hepatic cords. At 2 weeks posttreatment, Ad-leptin-treated (FIG. 8F) mice display a similar, but less pronounced hepatic pathology. The cellular infiltration observed resolved by the fourth week posttreatment; there is almost an absence of lesions in the Ad-leptin treated (FIG. 8H) mice, with only a trace of individual cell death present, which is within normal ranges. Examination of liver sections obtained from ob/ob mice reflected similar Ad-vector associated histopathology. Similar to the observations in lean mice, evidence of toxicity associated with Ad vectors was not observed with HD-leptin treatment in ob/ob mice, however, a slight cellular infiltrate was detected, which may be attributed to the immunogenicity of leptin in these leptin-deficient mice. Nonetheless, the extent of inflammation and cellular infiltrates remained significantly less than that observed with Ad-leptin (data not shown).

Figure 9:
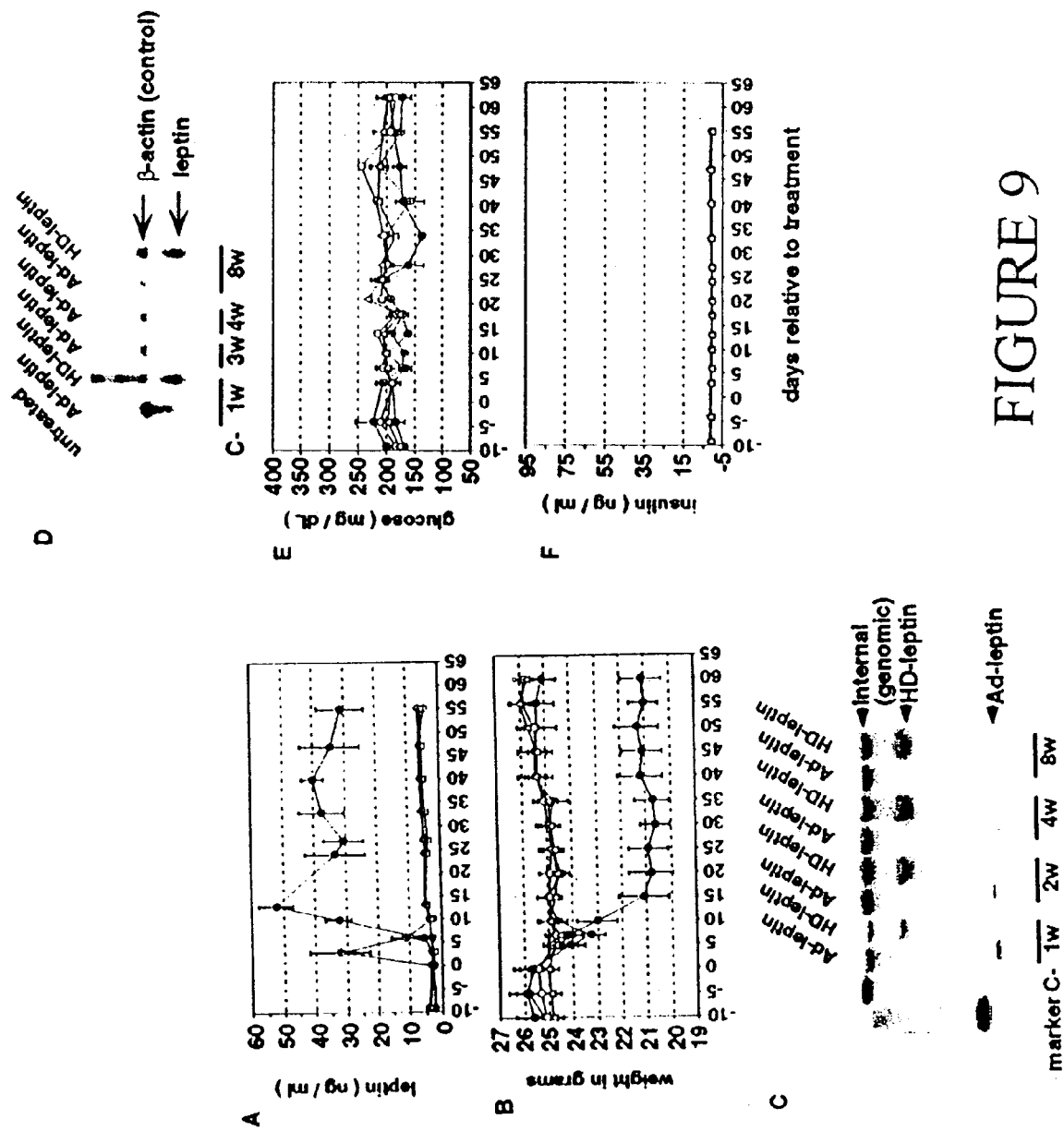
FIG. 9 shows HD-leptin and Ad-leptin effects in lean mice. Animals were injected via the tail vein with a single dose of $1-2 \times 10^{11}$ particles of HD-leptin (n=5), Ad-leptin (n=10), Ad-β-gal (n=10), or the equivalent volume of dialysis buffer (n=10). The time course shows (A) serum leptin levels, collected 2–3 times weekly (ng/ml, mean±SEM); (B) weight (g, mean±SEM); (C) Southern blot analysis, the arrows refer to the single HD-leptin and Ad-leptin bands. Three internal genomic bands were also detected in treated and control DNA: one strong (uppermost, greater than 12 kb), and two faint (lower) bands. (D) Total RNA from livers of Ad-leptin-treated mice at 1-, 2-, 4-, and 8-week intervals, and at 1 and 8 weeks in HD-leptin treated mice. Arrows refer to the leptin message (≈500 bp) band, β-actin was used as the internal control (≈1 kb). E and F) Serum glucose (mg/dl) and insulin (ng/ml) were measured in all animal groups (mean±SEM).

In the lean mice, treatment with Ad-leptin resulted in a transient increase in serum leptin levels and weight loss that lasted for only 7–10 days (FIG. 9A and B). In contrast, treatment with HD-leptin resulted in high serum leptin levels (6- to 10-fold over background) and ≈20% weight loss that persisted at least 2 months (FIG. 9A and B). Weight loss in HD-leptin-treated mice was associated with satiety that persisted over a longer period (2–3 weeks, data not shown) than in those treated with Ad-leptin (5–7 days) (Morsy, M. A., Gu, M., Zhao, J. Z., Holder, D. J., Rogers, I. T., Pouch, W., Motzel, S. L., Klein, H. J., Gupta, S. K., Liang, X., et al. (1998) Gene Ther. 5, 8–18.). Vector DNA in the livers of Ad-leptin treated mice was rapidly lost and fewer than 0.2 copy per cell was detected, compared with 1 or 2 copies per cell after HD-leptin treatment at 8 weeks postinjection (FIG. 9C). These effects can be correlated with the duration of gene expression obtained with these two vector types. Gene expression mediated by Ad-leptin was transient and almost undetectable as early as 1 week posttreatment as seen by northern blot analysis of total liver RNA, whereas that mediated by HD-leptin persisted for at least eight weeks (FIG. 9D). No changes in serum glucose or insulin levels in the treated lean mice were detected throughout the study (FIGS. 9E and F). Vector DNA levels were stable at 1 to 2 copies per cell at 1, 2, 4, and 8 weeks posttreatment.

Figure 10:
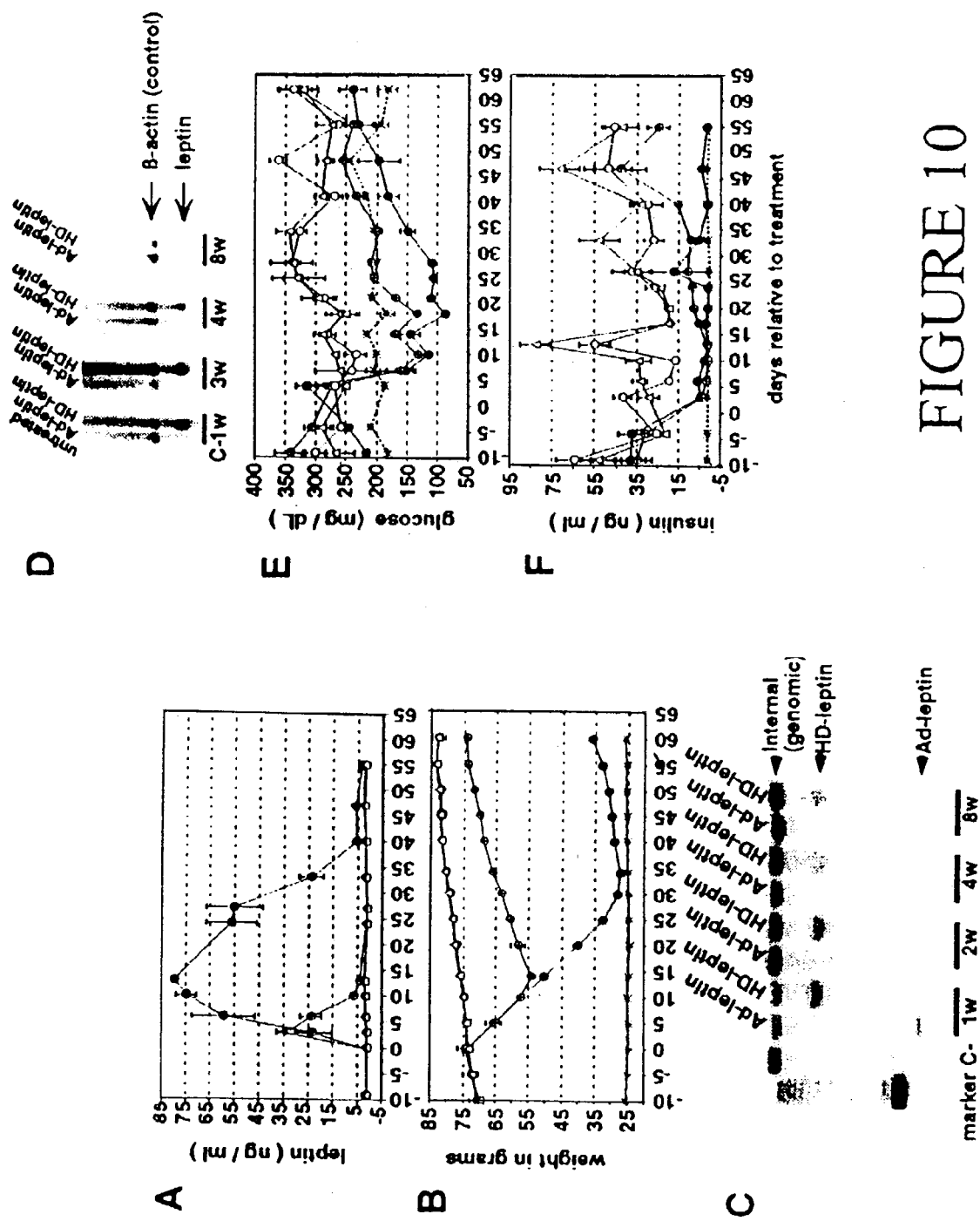
FIG. 10 shows HD-leptin and Ad-leptin effects in ob/ob mice. Essentially as described in FIG. 9, animals were injected in the tail vein with a single dose of $1-2 \times 10^{11}$ particles of HD-leptin (n=5), Ad-leptin (n=10), and Ad-β-gal (n=10), or the equivalent volume of dialysis buffer (n=10). Lean control values are plotted for comparison. The time course shows (A) serum leptin levels (ng/ml, mean±SEM), collected 2–3 times; (B) weight (g, mean±SEM). (C) Southern blot analysis, the arrows refer to the single HD-leptin and Ad-leptin bands. Three internal genomic bands were also detected in treated and control DNA: one strong (uppermost, >12 kb), and two faint (lower) bands. (D) Total RNA from livers of Ad-leptin-treated mice at 1-, 2-, 4-, and 8-week intervals, and in untreated mice. Arrows refer to the leptin message (≈500 bp) band, β-actin was used as the internal control (≈1 kb). (E and F) Serum glucose (mg/dl) and insulin (ng/ml) were measured in all animal groups (mean±SEM).
Figure 11:
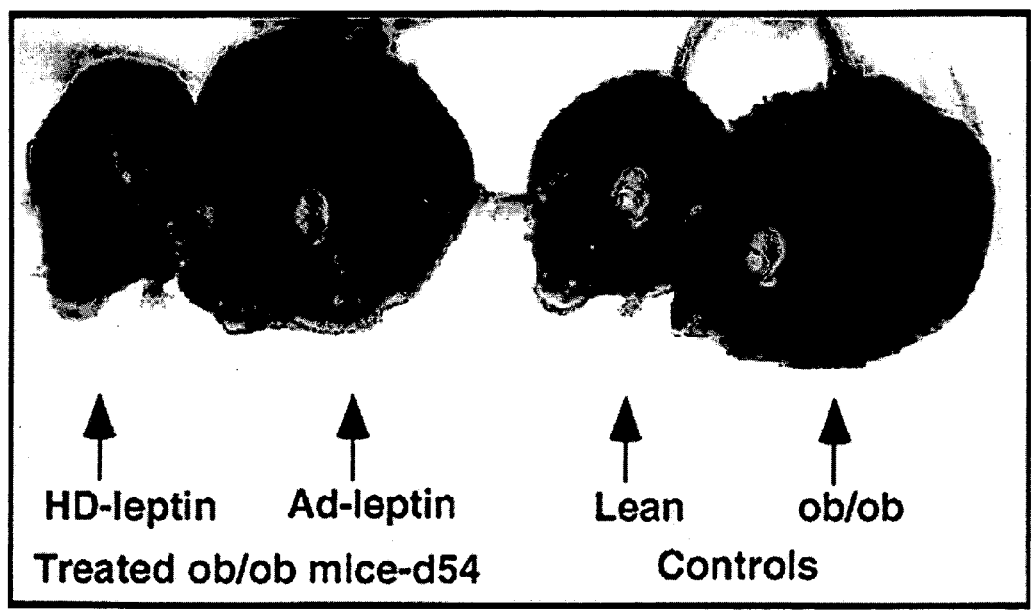
FIG. 11 shows phenotypic correction of HD-leptin-treated ob/ob mice. On the left is a representative ob/ob mouse treated with HD-leptin at day 54 posttreatment, next to a littermate treated with Ad-leptin. The Ad-leptin treated mouse initially lost weight during the first 2 weeks after the treatment, and subsequently gained weight. At 54 days post-Ad-leptin treatment, ob/ob mice are indistinguishable from untreated ob/ob control littermates, whereas HD-leptin-treated mice remained indistinguishable from untreated lean control mice. Untreated ob/ob and lean control mice are shown for comparison as labeled.

The ob/ob mice are naïve to leptin and thus transgene immunogenicity is not an unexpected finding. In these animals, similar to what was observed in the lean mice, HD-leptin was found to be more effective than the first-generation Ad-leptin vector. In the ob/ob treated with Ad-leptin, serum levels of leptin increased only for a short period during the first 4 days of treatment, returning to baseline levels within 10 days of postinjection (FIG. 9A). Increased leptin levels were associated with transient body weight loss of ≈25%, followed by weight gain, 2 weeks after treatment (FIGS. 10A and B). Similar to the results obtained in lean mice, the Ad-leptin vector DNA (FIG. 10C) was also rapidly lost (<0.2 copy per cell were detected by 2 weeks posttreatment, and undetectable by 8). In contrast, the ob/ob HD-leptin-treated mice had increased serum leptin levels up to ≈15 days posttreatment, after which the levels gradually dropped to baseline over the subsequent 25 days (FIG. 10A). The initial rise in leptin levels correlated with rapid weight reduction resulting in >60% weight loss (reaching normal lean weight) by 1 month (FIG. 10B). Weight loss was maintained for a period of 6–7 weeks posttreatment. As leptin levels dropped to baseline, a gradual increase in body weight was observed. Satiety was observed in association with increased leptin levels, and appetite suppression was sustained for a longer period (≈1 month) compared with the short transient effect induced by Ad-leptin (≈10 days) (data not shown). Leptin-specific antibodies were detected in the sera of ob/ob Ad-leptin and HD-leptin-treated mice (data not shown); therefore, it was essential to determine whether the drop observed in serum leptin levels was due to interference of the antibodies with the ELISA assay used to measure leptin or a loss of vector DNA and/or gene expression. Although by Southern blot analysis greater stability of HD-vector DNA was observed over Ad-vector DNA in livers of ob/ob treated mice compared at similar time points, the analysis revealed eventual loss of the HD-vector DNA over the 8 week time interval (FIG. 10C). Approximately 75% less vector DNA was detected in the livers of HD-leptin-treated ob/ob mice at 4 and 8 weeks posttreatment compared with the persistent levels found in the livers of HD-leptin-treated lean littermates at similar time points (FIGS. 10C and 9C repectively). Gene expression in ob/ob Ad-leptin treated mice correlated with the DNA findings, RNA levels were below the sensitivity level of detection at 1 week posttreatment, whereas in HD-leptin-treated mice, gene expression was detectedup to 4 weeks postinjection and was undetectable at 8 weeks (FIG. 10D). Serum glucose and insulin levels dropped during the first one or two weeks posttreatment to normal lean values in both HD-leptin- and Ad-leptin-treated mice, although the effects of HD-leptin treatment were sustained for longer periods, which parallels what was seen with weight loss, satiety, DNA stability and leptin gene expression (FIGS. 10E and F). The subsequent increase in glucose and insulin levels in both vector treatments correlated with the drop observed in serum leptin levels and eventual loss of vector DNA. The overall HD-leptin mediated prolonged effect was also reflected in the accompanying phenotypic correction, which lasted longer than that seen in litter mates treated with Ad-leptin (6–7 vs. 2–3 weeks) (FIG. 11).

It has been reported that Ad vectors and/or immunogenic transgenes can be associated with cytotoxic T lymphocyte cell responses that result in elimination of vector DNA infected cells and loss of gene expression (Yang, Y., Nunes, F. A., Berencsi, K., Furth, E. E., Gonczol, E. & Wilson, J. M. (1994) *Proc. Natl. Acad. Sci.* USA 91, 4407–4411.; Yang, Y., Ertl, H. D. & Wilson, J. M. (1995) *J. Virol.* 69, 2004–2015.; Lochmuller, H., Petrof, B. J., Pari, G., Larochelle, N., Dodelet, V., Wang, Q., Allen, C., Prescott, S., Massie, B., Nalbantoglu, J., et al. (1996) *Gene Ther.* 3, 706–716.; Gahery-Segard H., Juilliard, V., Gaston, J., Lengagene, R., Pavirani, A., Boulanger, P. & Guillet, J. G. (1997) *Eur. J. Immunol.* 27, 653–659.; Kajiwara, K., Byrnes, A. P., Charlton, H. M., Wood, M. J. & Wood, K. J., (1997) *Hum. Gene Ther.* 8, 45–56.; Kaplan, J. M., Armentano, D., Sparer, T. E., Wynn, S. G., Peterson, P. A., Wadsworth, S. C., Couture, K. K, Pennington, S. E., St. George, J. A., Gooding, L. R. & Smith, A. E. (1997) *Hum. Gene Ther.* 8, 45–46.; Worgall, S., Wolff, G., Falck-Pedersen, E. & Crystal, R. G. (1997) *Hum. Gene Ther.* 8, 37–44.; Tripathy, S. K., Black, H. B., Goldwasser, E. & Lieden, J. M. (1996) *Nat. Med.* 2, 545–550.). In some cases the response is influenced by the mouse strain used (Tripathy, S. K., Black, H. B., Goldwasser, E. & Lieden, J. M. (1996) *Nat. Med.* 2, 545–550.). In this study we used littermates to control against strain variation in our comparisons of the Ad-vector vs. the HD-vector immunogenicity in both lean animals that normally express leptin and ob/ob nice that are leptin deficient. Our studies clearly illustrate that HD-leptin achieved a substantial improvement in the safety profile and longevity of gene expression over that achieved with the first-generation Ad-leptin vector. The differences observed in the extent of cellular infiltrate in the liver, together with the pronounced liver toxicity as measured by ≈10- and 5-fold increases in AST and ALT serum values, respectively, associated with Ad-leptin but not HD-leptin treatment in lean mice, can be directly attributed to the elimination of the Ad protein-coding DNA sequences, because the leptin expression cassette was identical in both vectors. The appearance of a leptin-specific antibody response, gradual loss of gene expression and vector DNA observed in the ob/ob (leptin-deficient) but not in the lean mice (leptin-wild type) treated with HD-leptin may suggest an independent immune response event related to leptin tolerance.

The leptin model used in these studies provided a very instructive animal model to investigate the influence of both vector design and transgene product on the duration of expression after gene transfer. The differences between the longevity of expression mediated by the HD-deleted vector in the lean mice in this study and the very short lived effects reported by others may reflect variations in the vector construction features (Lieber, A., He, C., Kirillova, I. & Kay, M. A. (1996) *J. Virol.* 70, 8944–8960; Sykes, R. C., Lin, D., Hwang, S. J., Framson, P. E. & Chinault, A. C. (1998) *Mol. Gene. Genet.I* 212, 301–309.).

The HD-vector system is a significant advance over existing Ad vectors with regards to safety and insert capacity (up to 37 kb). In addition to the gain of these two valuable properties, the HD vectors have not lost the features that contributed to the general attractiveness of Ad vectors that include: (i) efficient in vivo gene delivery, and (ii) high titer production. The concatamerization of the 16.7 vector fragment to generate a ≈33 kb recombinant virus is a phenomenon that has been previously observed by others (Fisher, K. J., Choi, H., Burda, J., Chen, S. & Wilson, J. M. (1996) *Virology* 217, 11–22; Parks, R. J., & Graham, F. L. (1996) *J. Virol.* 71, 3293–3298.). The recombinant virus preferentially propagates at higher efficiencies when its genome length is at least 75% that of wild type (Parks, R. J., & Graham, F. L. (1996) *J. Virol.* 71, 3293–3298.). And although we detected traces of propagated 16.7 kb HD-leptin, the prevalence of this species was overwhelmingly surpassed by the 33-kb recombinant vector (FIG. 6B, Vector DNA A).

Replacements of leptin by other transgenes in the pΔSTK120 are ongoing to determine the universality of this vector backbone. The generation of other backbones with the duplicated left arm is being tested to determine the extent to which the two copies of packaging signal sequences is contributing to the efficient propagation and possible advantage of the HD-recombinant virus over the helper virus leading, to the exceedingly low levels of helper contamination in the HD stocks. The unique characteristics of HD-leptin together with the utilization of the 293-cre4 cells and the lox containing helper virus provides a biological method for generation of highly purified HD vectors. These advanced vectors improve the prospect of Ad vehicles for wide application in clinical gene therapy.

EXAMPLE 2

Figure 12:
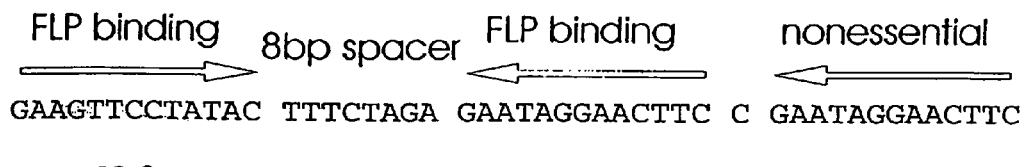
FIG. 12 Structure of FRT, the DNA recognition sequence acted upon by FLP and a summary of the properties of FLP.
Figure 13:
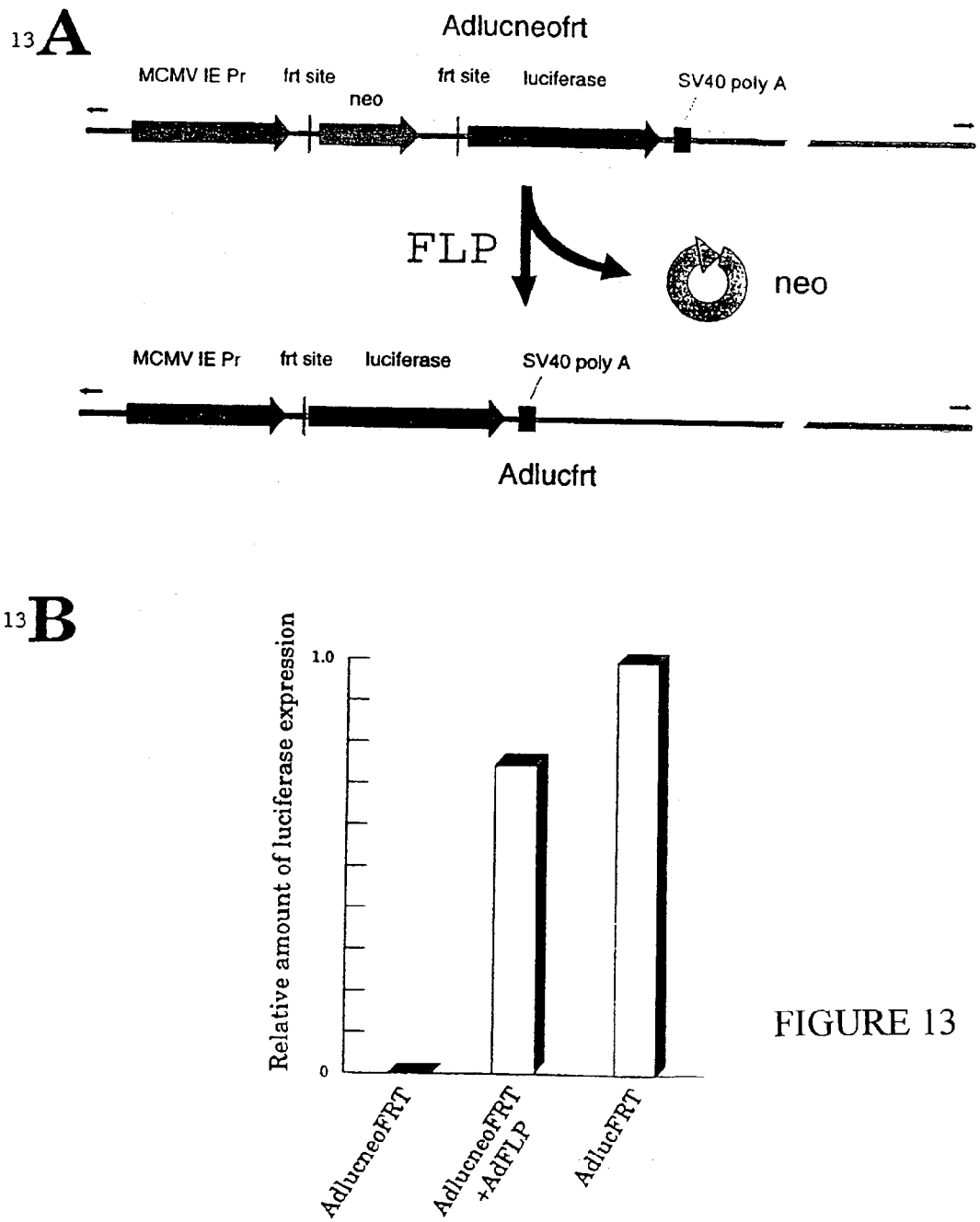
FIG. 13A A schematic diagram showing the structure of Adlucneofrt, an Ad vector encoding a luciferase expression cassette regulated by a "molecular switch" controlled by FLP mediated recombination.
FIG. 13B Results of an experiment designed to demonstrate FLP mediated recombination resulting in excision of a DNA segment flanked by FRT sites from Ad DNA.

The minimal FRT DNA sequence is a 34 bp DNA segment that is readily produced as a synthetic deoxyoligonucleotide that can be inserted into plasmid or viral DNA (see FIG. 12). To develop a simple and sensitive assay for FLP activity we constructed an adenovirus vector designated Adlucneofrt that contains an expression cassette comprising the murine cytomegalovirus immediate early gene promoter (MCMV IE Pr) followed by a DNA segment containing the neomycin resistance gene (neo) followed by the coding sequences for firefly luciferase and an SV40 polyadenylation signal. The neo sequences inserted between the MCMV IE PR and luciferase were flanked by FRT sites and were designed to prevent expression of luciferase unless said neo sequences are excised by the site specific recombinase FLP. The structure of Adlucneofrt and the effect of FLP mediated recombination are illustrated in FIG. 13A. Removal of neo from the Adlucneofrt genome generates a new viral DNA, Adlucfrt, that is rendered capable of expressing luciferase at high levels. As luciferase can be detected readily and with high sensitivity by standard assays, the system provides a simple and quantifiable assay for expression of FLP and for ability of FLP to excise DNA segments from the Ad genome when said DNA segments are flanked by FRT sites. A typical experiment in which cells were infected with Adlucneofrt or Adlucfrt or were coinfected with Adlucneofrt and AdFLP and cell extracts were subsequently prepared and assayed for luciferase activity is shown in FIG. 13B. AdFLP is an Ad vector that contains a FLP gene under the control of the human cytomegalovirus immediate early gene promoter that was obtained from Dr. Volker Sandig (Merck & Co., Inc.). The FLP gene can be cloned and expressed according to methods known in the art. As can be readily seen from the results depicted in FIG. 13B, no luciferase activity was detected in cells infected with Adlucneofrt, but activity was readily detected in cells coinfected with Adlucneofrt and AdFLP and the activity in said cells was more than 75% of that expressed in cells infected with Adlucfrt. These results are comparable to results obtained using Cre and lox (Anton, M. and Graham, F. L. Site-specific recombination mediated by an adenovirus vector expressing the Cre recombinase protein: a molecular switch for control of gene expression. J. Virol. 69: 4600–4606, 1995) and indicate that FLP can efficiently excise from the Ad genome DNA segments that are flanked with FRT sites.

EXAMPLE 3

An independent measure of the efficiency of excision of a DNA segment flanked by FRT sites was obtained by direct analysis of DNA structure using Southern blot analysis. Cells were infected with Adlucneofrt, Adlucfrt or were coinfected with Adlucneofrt and AdFLP and DNA was extracted 27 h post infection, digested with StuI or HindIII restriction enzymes, and transferred onto nitrocellulose membranes and probed with a labelled DNA that hybridized to neo and luciferase sequences. The structures of the Adlucneofrt virus and the probe are illustrated in FIG. 14A along with the structures of the products of FLP mediated recombination. The results of Southern blot hybridization analysis are presented in FIG. 14B. It is readily apparent from the DNA patterns in lanes 4, 7, 11 and 14 representing cells that were coinfected with Adlucneofrt and AdFLP that most of the Adlucneofrt DNA had undergone FLP mediated recombination to generate a left end StuI fragment of 6008 bp (lanes 4 and 7) or a left end HindIII fragment of 6468 bp (lanes 11 and 14) plus a small amount of a 348 bp fragment representing the excised neo fragment.

EXAMPLE 4

Figure 15:
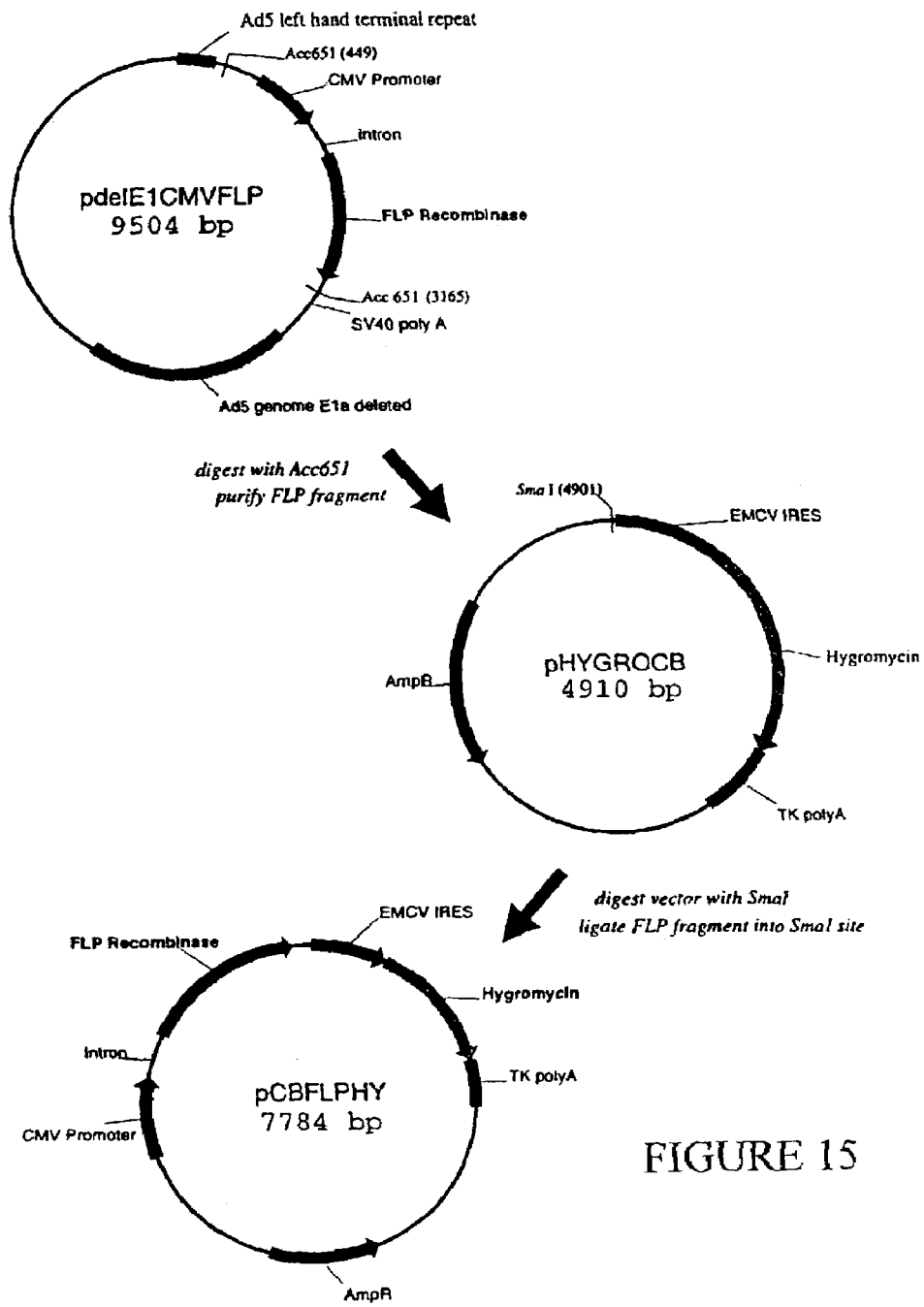
FIG. 15 illustrates the construction of a plasmid, pCB-FLPHy, that contains an expression cassette encoding FLP and hygromycin resistance for transformation of mammalian cells.
Figure 16:
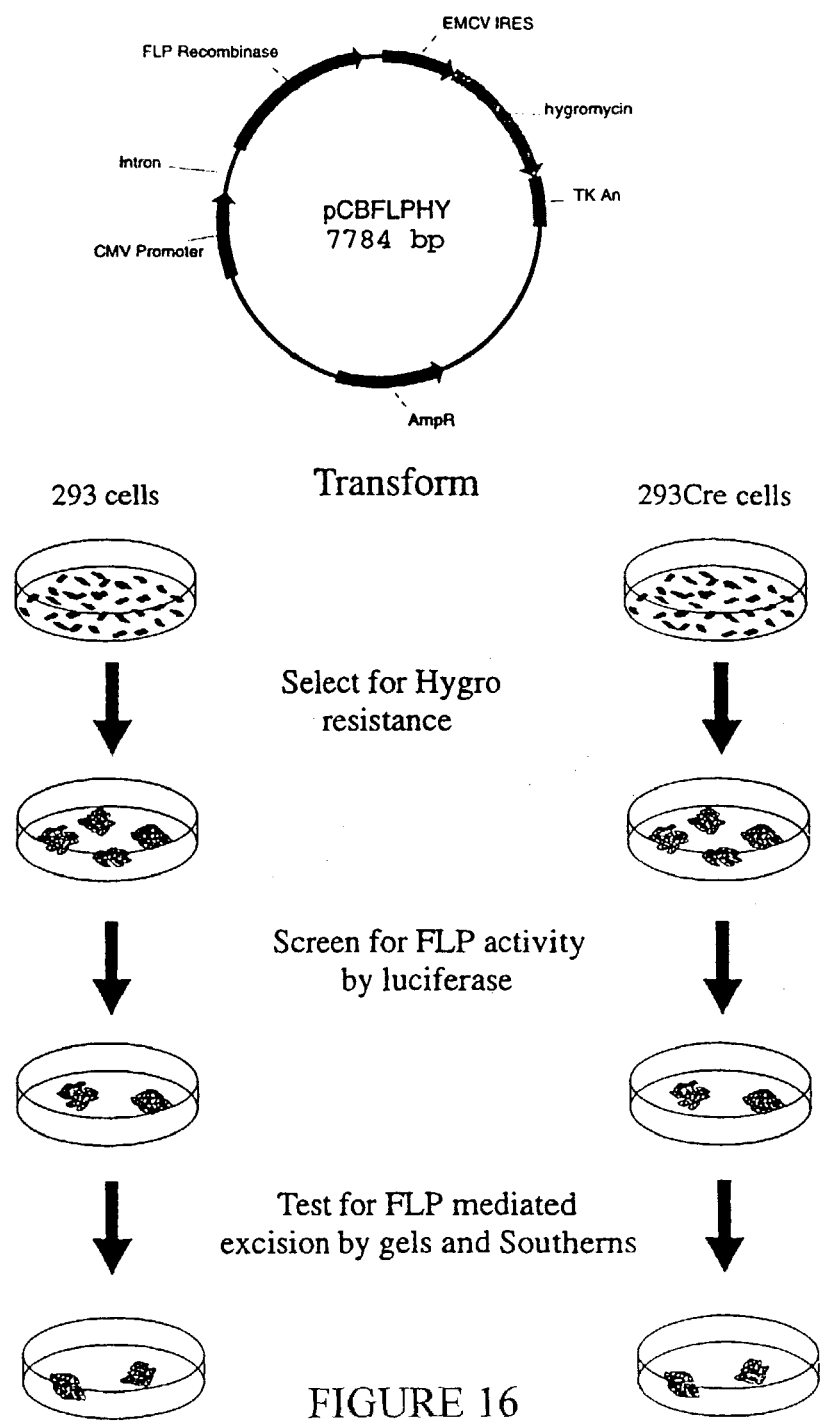
FIG. 16 is a diagrammatic representation of a means to obtain 293 and 293Cre cell lines that express FLP recombinase.

Plasmids were constructed containing FLP recombinase and encoding hygromycin resistance for transformation of cells to obtain cell lines expressing high concentrations of FLP. In the example illustrated in FIG. 15 the plasmid pde1EICCMVFLP (obtained from Dr. Volker Sandig, Merck Inc.) was digested with Acc651 and the fragment containing the FLP gene was treated with the Klenow fragment of *E. coli* DNA polymerase and ligated into the Sma I site of pHYGROCB to generate pCBFLPHY. The plasmid pCBFLPHY encodes a bicistronic expression cassette that expresses both hygromycin resistance and FLP under the control of the HCMV IE gene promoter. Therefore transfection and subsequent selection for cells resistant to hygromycin results in strong selection for cells that coexpress FLP recombinase. This example is not meant to be limiting as one skilled in the art will readily appreciate that other configurations or combinations of the FLP gene and hygromycin genes and other promoters could be used or cells could be cotransfected with separate plasmids encoding FLP and hygromycin or different selectable genes could be employed other than that encoding hygromycin resistance.

EXAMPLE 5

Figure 17:
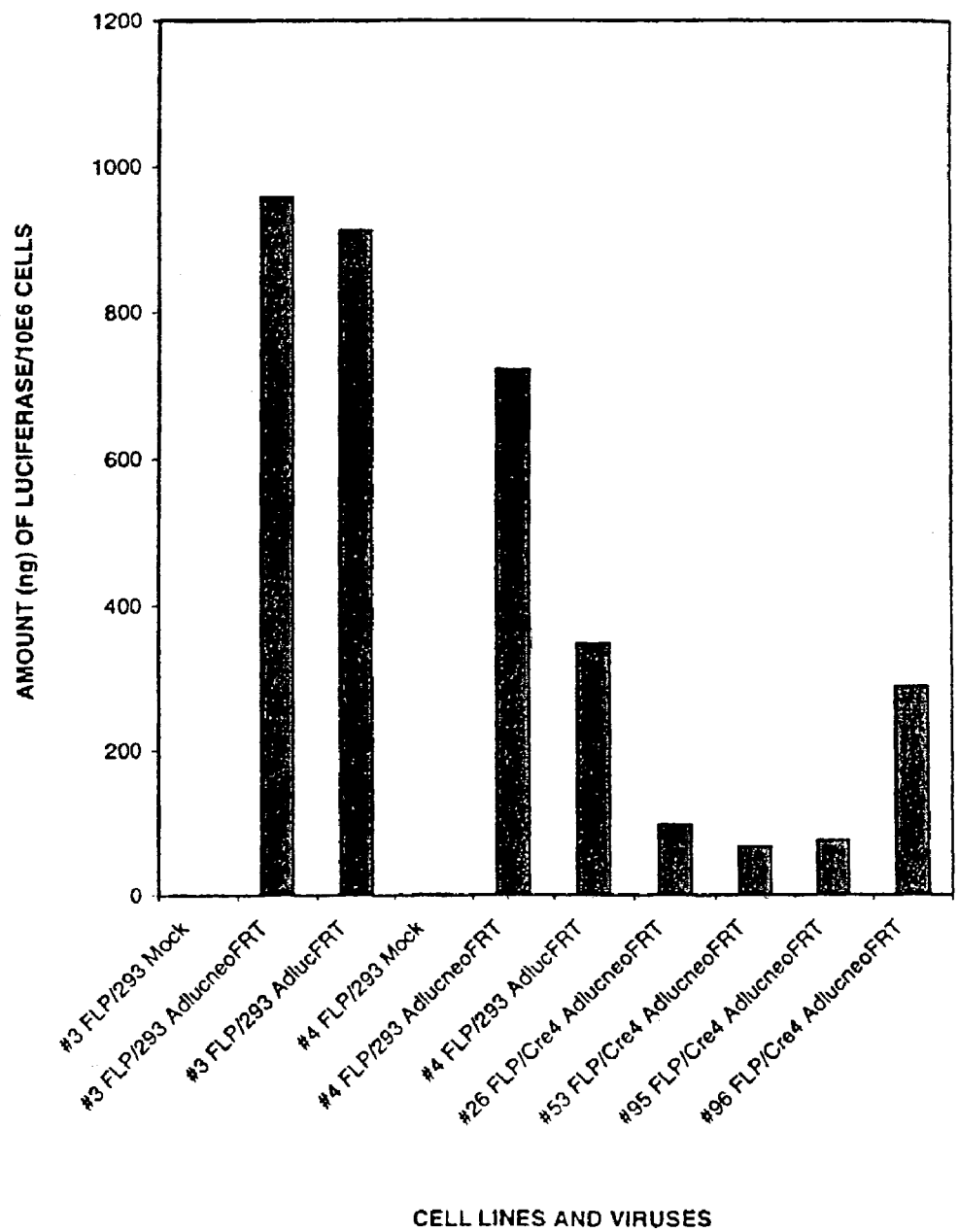
FIG. 17 is a schematic diagram showing the results of an experiment designed to screen for FLP expressing transformed cells by infection with Adlucneofrt and assay of luciferase expression.

293 and 293Cre cells were transfected with pCBFLPHY and selected for hygromycin resistance by incubation in hygromycin at various concentrations ranging from 200 to 600 μg/ml. Transformed colonies were isolated and expanded and screened for FLP expression using the assay described in Example 2. Results of a typical experiment are illustrated in FIG. 17, which shows the results of luciferase assays of cell extracts prepared from various cells infected with AdlucneoFRT from which luciferase expression is dependent on FLP mediated excision of neo sequences embedded between the promoter and the luciferase cDNA. It can be readily seen that in all cell lines assayed (#3FLP293, #4FLP293, #26FLP293Cre4, #53FLP293Cre4, #95FLP293Cre4, #96FLP293Cre4) readily detectable FLP activity was expressed and in several lines, (eg. #3FLP293, #4FLP293, #96FLP293Cre4), levels of luciferase expression are comparable to those induced by the control vector AdlucFRT, that has only a single FRT site between the HCMV promoter and the luciferase cDNA, and which has a structure identical to that generated by FLP mediated recombination of FRT sites in AdlucneoFRT (see FIG. 13A). Thus FLP expressing cell lines can be readily generated by transformation of 293 and 293Cre4 cells with pCBFLPHY. These examples are not limiting as numerous other cell lines have been generated, and one skilled in the art would not be limited to the use of 293 or 293Cre, cells but could equally use pCBFLPHY or like plasmids to transform other human or other mammalian cell lines to obtain cells expressing FLP.

EXAMPLE 6

Figure 18:
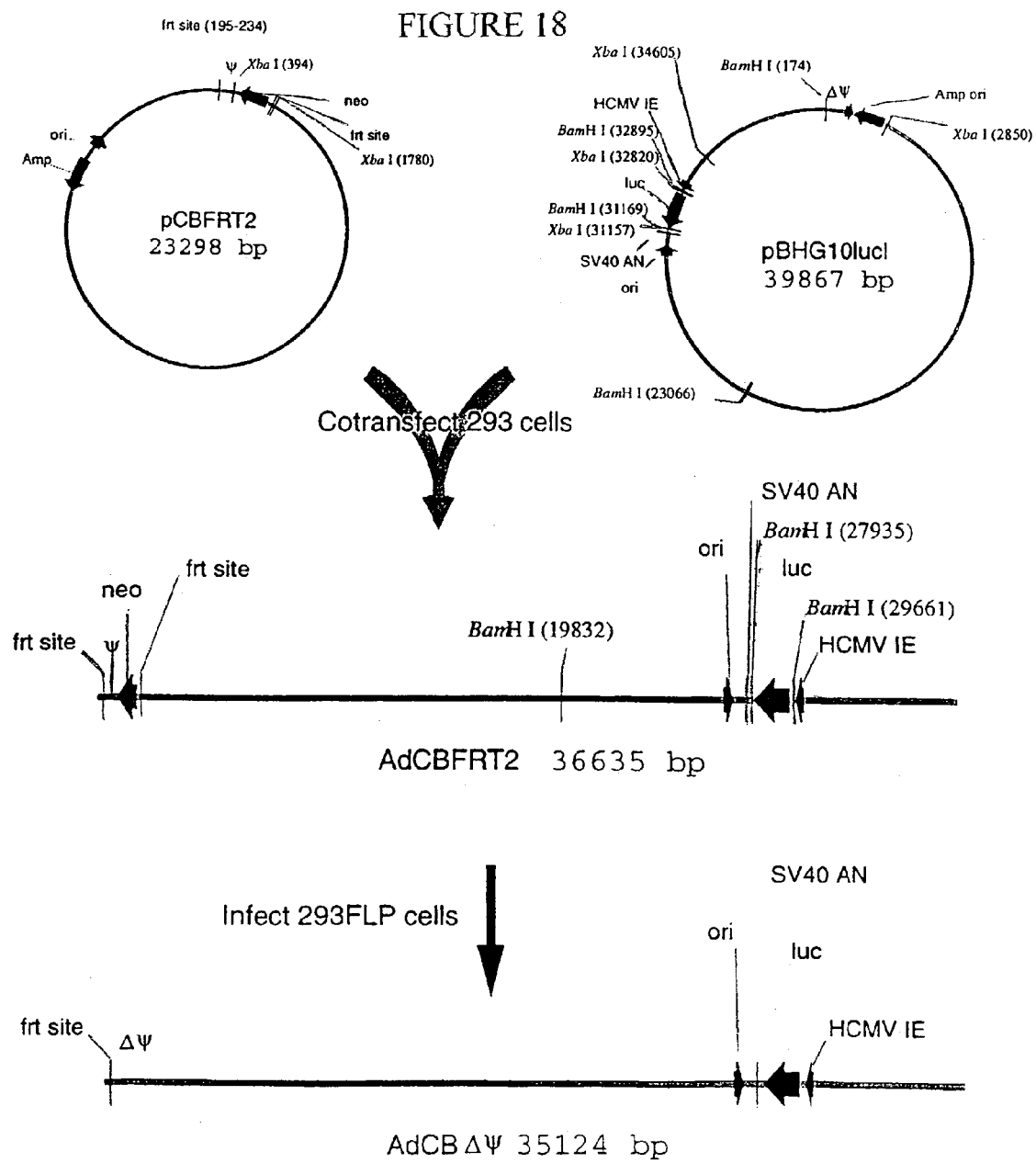
FIG. 18 illustrates construction of a helper virus, AdCBFRT2, that contains a packaging signal and neo sequences flanked by FRT sites, and showing the effect of FLP mediated excision of the "FRTed" sequences.
Figure 19:
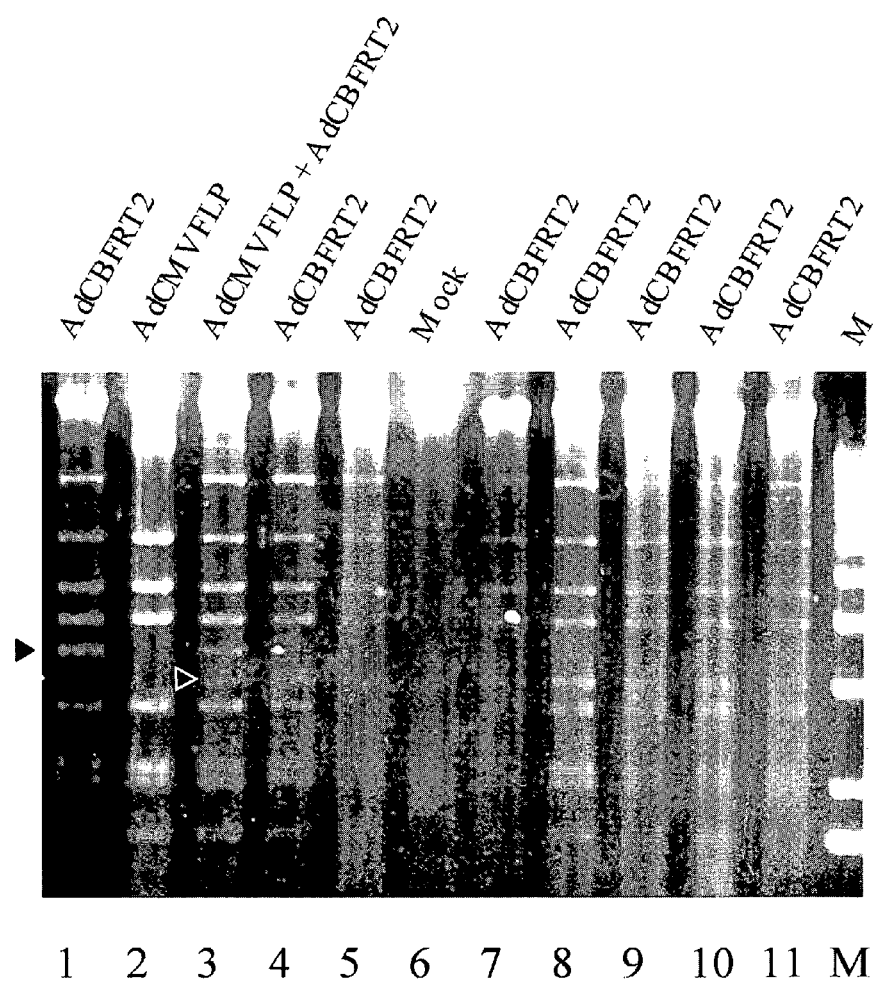
FIG. 19 illustrates restriction enzyme and agarose gel electrophoretic analysis of DNA extracted from cells infected with AdCBFRT2 showing excision of DNA sequences flanked by FRT sites by FLP mediated recombination.

To produce a helper virus containing a packaging signal flanked by FRT sites the method illustrated in FIG. 18 was used. A plasmid, pCBFRT2, was constructed that contains FRT sites on either side of the packaging signal, Ψ, plus for ease of analysis of products of FLP mediated recombination, a DNA sequence from the neo gene. Plasmid pCBFRT2 was constructed from pLC4 by methods essentially identical to those used to construct analogous plasmids containing loxP sites as described in: Parks, R. J., Chen, L., Anton, M., Sankar, U., Rudnicki, M. A. and Graham, F. L. A new helper-dependent adenovirus vector system: removal of helper virus by Cre-mediated excision of the viral packaging signal. Proc. Natl. Acad. Sci. U.S. 93: 13565–13570, 1996 and was cotransfected into 293 cells with pBHG10lucl (as described in Parks et al, ibid) to produce AdCBFRT2. Additional helper viruses were isolated by first removing neo from pCBFRT2 and cotransfecting the resulting plasmid with pBHG10lucl or similar pBHG10 plasmids containing other stuffer sequences in E3. The left end of AdCBFRT2 is essentially identical to that of AdLC8cluc (ibid) except that where the latter has loxP sites the former has FRT sites. Excision of the AdCBFRT2 DNA flanked by FRT sites as would occur in 293 cells expressing FLP recombinase generates a helper virus DNA that is capable of replicating and expressing viral functions needed for viral DNA replication and virion assembly but is not itself packaged into virions, as amply documented in Parks et al, 1996. The efficiency of excision of the "FRTed" packaging signal of AdCBFRT2 after infection of various 293FLP and 293Cre-FLP cell lines isolated as described in EXAMPLE 5 was assessed by Pvu I restriction of inflected cell DNA and agarose gel electrophioresis. The results are illustrated in FIG. 19. Pvu I digestion of AdCBFRT2 produces two fragments from the left end of 1112 and 3479 bp. The 1112 bp fragment is not shown but the 3479 bp fragment is indicated by the closed arrow left of lane 1. After FLP mediated recombination, AdCBFRT2 DNA is converted to AdCBΔΨ as illustrated at the bottom of FIG. 18. Pvu I digestion of AdCBΔΨ produces a single fragment from the left end of 3081 bp as a result of the excision of 1511 bp of "FRTed" DNA including the packaging signal and a Pvu I site. This fragment is indicated by the open arrow to the left of lane 3. Lanes 1, 2 and 3 contain DNA extracted 60 hrs post infection from 293Cre4 cells infected with 5 PFU/cell of, respectively, AdCBFRT2, AdCMVFLP, and AdCBFRT2+AdCMVFLP. Lanes 4 & 5 contain DNA extracted from FLP expressing 293 cells, lines 3 & 4 (transformed by pCBFLPHY). Lane 6 contains uninfected 293Cre4 DNA, and lanes 7–11 contain DNA from 293Cre4 cells transformed by pCBFLPHY, lines 12, 27, 34, 75 and 94 respectively. It can be readily seen from examination of the gel that coinfection of cells with AdCBFRT2+AdCMVFLP results in partial excision of the "FRTed" DNA of AdCBFRT2, infection of the FLP expressing 293 and 293Cre sublines with AdCBFRT2 resulted in essentially complete excision of the packaging signal as the 3479 bp fragment has become undetectable and is replaced by its 3081 bp recombination product.

Figure 20:
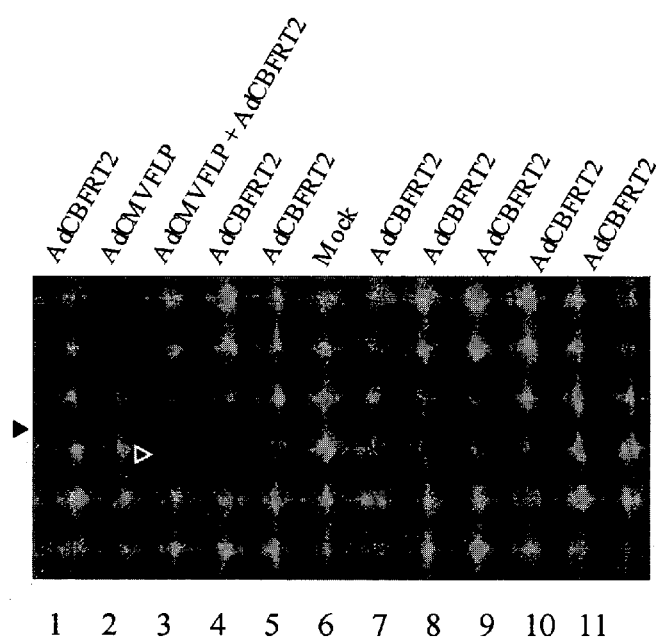
FIG. 20 Results of Southern blot hybridization analysis of DNA extracted from cells infected with AdCBFRT2.

Further study of the DNA structure in the virus infected cells was carried out by Southern blot analysis of the gel shown in FIG. 19. DNA was transferred onto nitrocellulose membranes and probed with a labelled DNA that hybridized to Ad sequences from the right most FRT site to the PvuI site at nt 6261. The results of Southern blot hybridization analysis are presented in FIG. 20 and confirm that FLP mediated excision of "FRTed" DNA sequences from AdCBFRT2 is highly efficient in all of the 293 or 293Cre cell lines that had been transformed by pCBFLPHY as evidenced by the disappearance of the 3479 bp fragment and appearance of the 3081 bp fragment corresponding to the left end Pvu I fragment from AdCBΔΨ.

Since all of the methodology described herein is essentially that employed in the production of the original 293 Cre cells and the results of all analyses are identical to results obtained with the Cre-lox system, and since there is ample space for insertion between the ITR and the packaging signal of a combination of loxP and FRT sites, and since we have demonstrated that 293Cre cells can be transformed to express FLP in addition to Cre, those skilled in the art will appreciate from the present disclosure that not only can 293 FLP cells be produced and used to excise sequences flanked by FRT sites, but 293 Cre/FLP cells can be produced and used to excise sequences flanked by lox sites, FRT sites or both, and in addition, cells may be produced which encode other recombinases for use with other site-specific recognition sites according to the present methodology. Thus constructs can be prepared wherein several site-specific recombinase target sites are used to flank a sequence, the excision of which is desired. LoxP sites flanking a first sequence, FRT sites flanking a second sequence, or loxP and FRT sites flanking a particular sequence are all strategies which may be employed, such that upon expression of the relevant recombinase, (Cre, FLP or like recombinase), the relevant sequence is excised. Use of multiple recognition sites and recombinases in a given construct provides redundancy and fail-safe methodology when certainty and high-efficiency target site excision is critical. Accordingly, this invention enables the production of FLP based helper viruses or FLP+Cre based helper viruses and vectors which employ Cre-FLP or other recombinase systems and combinations thereof.

What is claimed is:

1. An adenovirus vector system for expressing foreign DNA sequences, comprising:
   a. a helper adenovirus comprising a modified early region 1 (E1) wherein adenoviral packaging signals contained within said E1 region are flanked on both sides by site-specific recombinase target recognition sites other than lox sites;
   b. an integrase family recombinase other than Cre which catalyzes site-specific recombination between said site-specific recombinase target recognition sites; and,
   c. a helper-dependent adenovirus vector, comprising:
      i. a deletion of up to approximately 35,000 bp of adenoviral sequences but retaining sufficient right and left ITR sequences to support viral replication and packaging; and
      ii. foreign nucleic acid sequences of up to about 37,000 bp.

2. The recombinant adenovirus vector system according to claim 1, wherein said integrase family recombinase is FLP, and wherein said site-specific recombinase target recognition sites are FRT sites.

3. The recombinant adenovirus vector system according to claim 1 wherein said foreign nucleic acid sequences are comprised of two or more vector fragments that concatamerize to generate said helper-dependent adenovirus vector.

4. The recombinant adenovirus vector system according to claim 1, wherein said integrase family recombinase is expressed by a cell into which both said helper adenovirus and said helper-dependent adenovirus are introduced.

5. The recombinant adenovirus vector system according to claim 1, wherein said integrase family recombinase is encoded by said helper adenovirus, by said helper-dependent adenovirus vector, by both said helper adenovirus and said helper-dependent adenovirus vector, or wherein said integrase family recombinase is encoded by a third vector.

6. The recombinant adenovirus vector system according to claim 1, wherein the packaging signals of said helper adenovirus additionally are flanked on both sides by additional site-specific recombinase target recognition sites that are lox sites, and comprising an additional recombinase, wherein said additional recombinase is Cre.

7. A plasmid for making a helper adenovirus comprising a modified circular adenoviral genome having a modified early region 1 (E1) wherein adenoviral packaging signals contained within said E1 region are flanked on both sides by first site-specific recombinase target recognition sites other than lox sites, said sites corresponding to said first site-specific recombinase target recognition sites of a integrase family recombinase other than Cre.

8. The plasmid according to claim 7 further comprising a bacterial origin of replication, an antibiotic resistance gene, or both.

9. The plasmid according to claim 8, wherein said iniegrase family recombinase is FLP, and said site-specific recombinase target recognition sites are FRT sites.

10. The plasmid according to claim 9 further comprising second site-specific recombinase target recognition sites flanking said E1 region and corresponding to a second integrase family recombinase.

11. The plasmid according to claim 9 wherein said second recombinase is Cre, and said second site-specific rceombinase target recognition sites are lox sites.

12. A method for making a packaged helper-dependent adenovirus vector comprising co-infecting a cell with:
   a. at least one helper adenovirus comprising an E1 region wherein packaging signals contained within said E1 region are flanked on both sides by site-specific integrase family recombinase target recognition sites other than lox sites; and
   b. at least one helper-dependent adenovirus vector;
   wherein said cell supports replication of said at least one helper adenovirus and wherein said cell expresses a site-specific integrase family recombinase other than Cre, such that upon incubation of the co-infected cell, said recombinase catalyzes the removal of the packaging signals from said at least one helper adenovirus such that said least one helper adenovirus without packaging signals does not package, wherein said at least one helper adenovirus replicates, wherein said at least one helper adenovirus supports replication of said at least one helper-dependent adenovirus vector, and wherein said at least one helper-dependent adenovirus vector is packaged into adenovirus virions.

13. The method according to claim 12 wherein said integrase family recombinase is FLP, and wberein said site-specific integrase family recombinase target recognition sites are FRT sites.

14. The method according to claim 12 wherein each of said at least one helper-dependent vector comprises:
   a. a deletion of up to approximarey 35,000 bp of adenoviral sequences but retaining sufficient right and left ITR sequences to support viral replication and packaging; and
   b. foreign DNA sequences of up to about 37,000 bp.

15. The method according to claim 14 wherein said foreign DNA sequences are comprised of two or more vector fragments that concatamerize to form said helper-dependent vector.

16. A method for excising specific nucleic acid sequences from a helper adenovirus, which helper adenovirus supports replication of a helper-dependent adenoviral vector co-infected in a cell with said helper adenovirus, which comprises constructing said helper adenovirus such that said specific nucleic acid sequences are flanked on both sides wit site-specific integrase family recombinase target recognition sites other than lox, and contacting said helper adenovirus with a integrase family recombinase other tan Cre to induce excision of said specific nucleic acid sequences.

17. The method according to claim 16 wherein said inregrase family recombinase is FLP, and wherein said site-specific integrase family recombinase target recognition sites are FRT sites.

18. The method according to claim 16 wherein said integrase family recombinase is encoded by said helper adenovirus, by said helper-dependent adenovirus vector, by said cell, by a third vector, or by combinations thereof.

* * * * *

UNITED STATES PATENT AND TRADEMARK OFFICE
CERTIFICATE OF CORRECTION

| | | |
|---|---|---|
| PATENT NO. | : 7,045,347 B2 | |
| APPLICATION NO. | : 10/206163 | |
| DATED | : May 16, 2006 | |
| INVENTOR(S) | : Frank L. Graham et al. | |

It is certified that error appears in the above-identified patent and that said Letters Patent is hereby corrected as shown below:

Line 2 of claim 9, the word "iniegrase" should read -- integrase --.

Line 1 of claim 11, the claim reference numeral "9" should read --10 --; line 2 of claim 11, the hyphenated word part "rceombi-" should read -- recombi- --.

Line 14 of claim 12, add -- at-- between the words "said" and "least"; line 15 of claim 12, add -- replicates but -- between the words "signals" and "does"; line 16 of claim 12, remove the phrase "wherein said at least one helper adenovirus replicates,".

Line 3 of claim 14, the word "approximarely" should read -- approximately --.

Line 6 of claim 16, the word "wit" should read -- with --; line 9 of claim 16, the word "tan" should read -- than --.

Signed and Sealed this

First Day of May, 2007

JON W. DUDAS
*Director of the United States Patent and Trademark Office*

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Description of Combined DNA/RNA Molecule:PRIMER
<223> OTHER INFORMATION: Description of Artificial Sequence:Primer
      sequence for junction

```
<400> SEQUENCE: 1
ctcttcttct gtcacacccc tcccuc                                   26

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence:
      Yeast 2 micron FRT sequence

<400> SEQUENCE: 2
gaagttccta tactttctag agaataggaa cttccgaata ggaacttc           48
```